(12) United States Patent
Roukes et al.

(10) Patent No.: US 8,827,548 B2
(45) Date of Patent: Sep. 9, 2014

(54) POLYMER NEMS FOR CELL PHYSIOLOGY AND MICROFABRICATED CELL POSITIONING SYSTEM FOR MICRO-BIOCALORIMETER

(75) Inventors: Michael L. Roukes, Pasadena, CA (US); Chung-Wah Fon, Camarillo, CA (US); Wonhee Lee, Pasadena, CA (US); Hongxing Tang, Pasadena, CA (US); Blake Waters Axelrod, Sierra Madre, CA (US); John Liang Tan, San Diego, CA (US)

(73) Assignee: California Institute of Technology, Pasadena, CA (US)

( * ) Notice: Subject to any disclaimer, the term of this patent is extended or adjusted under 35 U.S.C. 154(b) by 423 days.

(21) Appl. No.: 13/110,684

(22) Filed: May 18, 2011

(65) Prior Publication Data
US 2011/0216804 A1  Sep. 8, 2011

Related U.S. Application Data

(62) Division of application No. 11/830,612, filed on Jul. 30, 2007, now Pat. No. 7,966,898.

(60) Provisional application No. 60/834,253, filed on Jul. 28, 2006, provisional application No. 60/834,052, filed on Jul. 28, 2006, provisional application No. 60/834,288, filed on Jul. 28, 2006.

(51) Int. Cl.
*G01K 17/02* (2006.01)
*G01N 25/20* (2006.01)

(52) U.S. Cl.
USPC ............................................. 374/31; 422/51

(58) Field of Classification Search
USPC ........ 435/287.1; 977/724, 956, 958; 600/531; 422/51; 374/31, 33
See application file for complete search history.

(56) References Cited

U.S. PATENT DOCUMENTS 4,711,820 A   12/1987  Arkles et al.
4,935,345 A *  6/1990  Guilbeau et al. ............... 435/14
(Continued)

FOREIGN PATENT DOCUMENTS

WO   94/28372   12/1994
WO   02/12443    2/2002
(Continued)

OTHER PUBLICATIONS

Zhang, Yuyan. A micromachined thermal sensor for biochemical sensing and polymer characterization. Dissertation, The Pennsylvania State University. Pennsylvania. ProQuest/UMI, 2005.*
(Continued)

*Primary Examiner* — Lisa Caputo
*Assistant Examiner* — Punam Roy
(74) *Attorney, Agent, or Firm* — Gates & Cooper LLP

(57) ABSTRACT

A microfluidic embedded nanoelectromechanical system (NEMs) force sensor provides an electrical readout. The force sensor contains a deformable member that is integrated with a strain sensor. The strain sensor converts a deformation of the deformable member into an electrical signal. A microfluidic channel encapsulates the force sensor, controls a fluidic environment around the force sensor, and improves the read out. In addition, a microfluidic embedded vacuum insulated biocalorimeter is provided. A calorimeter chamber contains a parylene membrane. Both sides of the chamber are under vacuum during measurement of a sample. A microfluidic cannel (built from parylene) is used to deliver a sample to the chamber. A thermopile, used as a thermometer is located between two layers of parylene.

10 Claims, 22 Drawing Sheets

(56) References Cited

U.S. PATENT DOCUMENTS

| | | |
|---|---|---|
| 6,408,878 B2 | 6/2002 | Unger et al. |
| 6,540,895 B1 | 4/2003 | Spence et al. |
| 6,575,020 B1 | 6/2003 | de Charmoy Grey et al. |
| 6,793,753 B2 | 9/2004 | Unger et al. |
| 6,899,137 B2 | 5/2005 | Unger et al. |
| 6,929,030 B2 | 8/2005 | Unger et al. |
| 7,040,338 B2 | 5/2006 | Unger et al. |
| 7,144,616 B1 | 12/2006 | Unger et al. |
| 7,169,314 B2 | 1/2007 | Unger et al. |
| 7,214,298 B2 | 5/2007 | Spence et al. |
| 7,216,671 B2 | 5/2007 | Unger et al. |
| 7,704,745 B2 * | 4/2010 | Baudenbacher et al. ....... 436/34 |
| 7,762,719 B2 * | 7/2010 | Fon et al. ................ 374/31 |
| 8,343,778 B2 * | 1/2013 | Yu et al. ................ 435/6.11 |
| 2004/0211243 A1 | 10/2004 | Porter et al. |
| 2005/0014129 A1 * | 1/2005 | Cliffel et al. .............. 435/4 |
| 2005/0204821 A1 * | 9/2005 | Fischer et al. ............ 73/715 |
| 2007/0286254 A1 * | 12/2007 | Fon et al. ............... 374/31 |
| 2010/0000292 A1 | 1/2010 | Karabacak et al. |
| 2010/0233792 A1 | 9/2010 | Begley et al. |

FOREIGN PATENT DOCUMENTS

| | | | |
|---|---|---|---|
| WO | 03/022731 | 3/2003 | |
| WO | 03/095616 | 11/2003 | |
| WO | 2005/119233 | 12/2005 | |
| WO | WO 2006073426 A2 * | 7/2006 | ............. G01K 17/00 |

OTHER PUBLICATIONS

E. A. Johannessen, J. M. R. Weaver, P. H. Cobbold, J. M. Cooper, "A suspended membrane nanocalorimeter for ultralow volume bioanalysis," IEEE transactions on Nanobioscience, vol. 1, No. 1, Mar. 2002.*

Y. S. Shin, K. cho, S. H. Lim, S. Chung, S.-J. Park, C. Chung, D.-C. Han, J. K. Chang, "PDMS-based micro PCR chip with parylene coating," J. Micromech. Microeng. 13 (2003) pp. 768-774.*

Roukes, M. Nanoelectromechanical systems face the future. Phys. World 14, 25-31 (Feb. 2001).

Cleland, A. N. & Roukes, M. L. A nanometre-scale mechanical electrometer. Nature 392, 160-162 (1998).

Rugar, D. et al. Single spin detection by magnetic resonance force microscopy. Nature 430, 329-332 (2004).

Yang, Y. T. et al. Zeptogram-scale nanomechanical mass sensing. Nano Lett. 6 (4), 583-586 (2006).

Mamin, H. J. & Rugar, D. Sub-attonewton force detection at millikelvin temperatures. Appl. Phys. Lett. 79 (20), 3358-3360 (2001).

Naik, A. et al. Cooling a nanomechanical resonator with quantum back-action. Nature 443, 193-196 (2006).

Schwab, K. C. & Roukes, M. L. Putting mechanics into quantum mechanics. Phys. Today 58, 36-42 (Jul. 2005).

Tortonese, M., Barrett, R. C. & Quate, C. F. Atomic resolution with an atomic force microscope using piezoresistive detection. Appl. Phys. Lett. 62 (8), 834-836 (1993).

Landau, L. D. and Lifshitz E. M. Theory of Elasticity (1959), pp. viii, 1-14, 64-81.

Thaysen, J. Yalcinkaya, AD, Vettiger, P., and Menon, A. Polymer-based stress sensor with integrated readout. J. Phys. D: Appl. Phys. 35, 2698-2703 (2002).

Mo Li, H. X. Tang, and M.L. Roukes, Ultra-sensitive NEMS-based cantilevers for sensing, scanned probe and very high-frequency applications, Nature Nanotechnology, vol. 2, Feb. 2007, 114-120 (Jan. 28, 2007).

D. Martin Knotter and T.J.J. (Dee) Denteneer, Etching Mechanism of Silicon Nitride in HF-Based Solutions, Journal of the Electrochemical Society 148 (3) F43-F46 (2001).

John L. Tan, Wendy Liu, Celeste M. Nelson, Srivatsan Raghavan, and Christopher S. Chen, Simple Approach to Micropattern Cells on Common Culture Substrates by Tuning Substrate Wettability, Tissue Engineering, vol. 10, No. 5/6, 865-872 (2004).

Milan Mrksich, Chrisopher S. Chen, Younan Xia, Laura E. Dike, Donald E. Ingber, and George M. Whitesides, Controlling cell attachment on contoured surfaces with self-assembled monolayers of alkanethiolates on gold, Proc. Natl. Acad. Sci. USA vol. 93, pp. 10775-10778 (Oct. 1996).

T.G.I. Ling, M. Beck, R. Bunk, E. Forsen, J.O. Tegenfeldt, A.A. Zakharov, L. Montelius, Fabrication and chacterization of a molecular adhesive layer for micro- and nanofabricated electrochemical electrodes, Microelectronic Engineering 67-68 (2003) 887-892.

Chun-Min Lo, Hong-Bei Wang, Micah Dembo, and Yu-li Wang, Cell Movement is Guided by the Rigidity of the Substrate, Biophyscial Journal, vol. 79, pp. 144-152 (Jul. 2000).

John L. Tan, Joe Tien, Dana M. Pirone, Darren S. Gray, Kiran Bhadriraju, and Christopher S. Chen, Cells lying on a bid of microneedles: An approach to isolate mechanical force, Proceedings of the National Academy of Sciences, vol. 100, No. 4, pp. 1484-1489 (Feb. 18, 2003).

Arkles, B., Tailoring Surfaces with Silanes, CHEMTECH, 7(12), 766-778 (1977).

van Ruitenbeek, J. M., Alvarez, A., Pineyro, I., Grahman, C., Joyez, P., Devoret, M. H., Esteve, D., and Urbina, C. Adjustable nanofabricated atomic sized contacts. Review of Scientific Instruments, 67 (1), 108-111 (1996).

Johannessen, E A, Weaver, J M, Cobbold, P H, Cooper, J M. Heat conduction nanocalorimeter for pl-scale single cell measurement. Appl. Phys. Lett., 80 (11), 2029-2031 (2002).

Zhang, Y, and Tadigadapa, S. Calorimetric biosensors with integrated microfluidics channels. Biosensors and Bioelectronics, 19, 1733-1743 (2004).

Baier, V., Highly sensitive thermopile heat power sensor for microfluid calorimetry of biochemical processes, Sensors and Actuators A 123-124 (2005) 354-359.

Zhang, Y. and Tadigadapa, S., Thermal characterization of liquids and polymer thin films using a microcalorimeter, Applied Physics Letters 86, 034101 (2005).

Gelest Data Sheet, Applying a silane coupling agent, 1999.

Partial International Search Report for International Application No. PCT/US2007/016975 filed on Jul. 30, 2007.

International Search Report dated Mar. 12, 2008, International application No. PCT/US2007/016975, International filing date Jul. 30, 2007.

Snow et al., Static deflection measurements of cantilever arrays reveal polymer film expansion and contraction, Journal of Colliod and Interface Science, vol. 316, pp. 687-693. Aug. 30, 2007.

* cited by examiner

FIG. 3
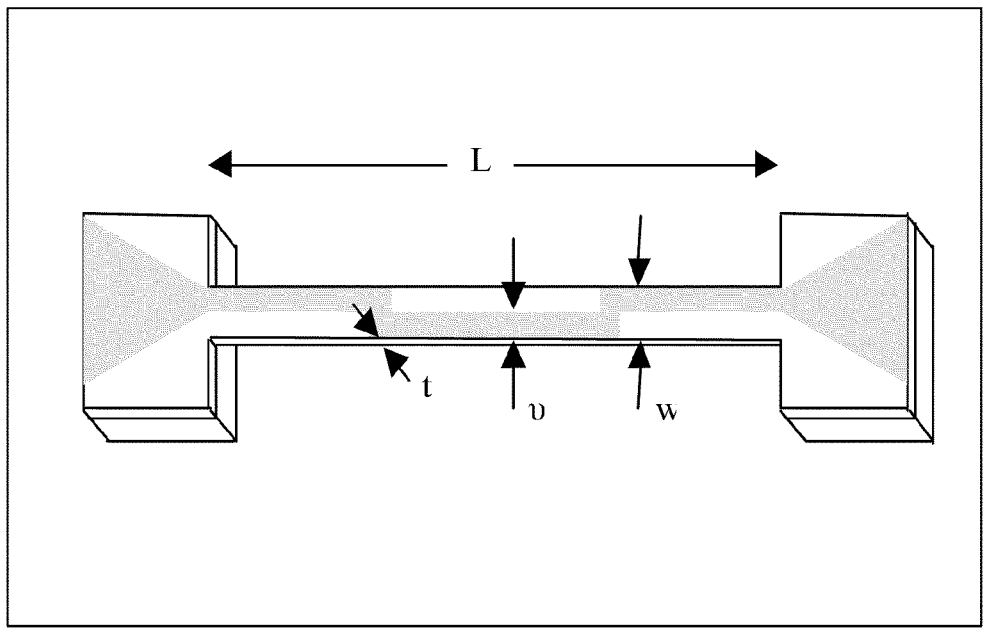
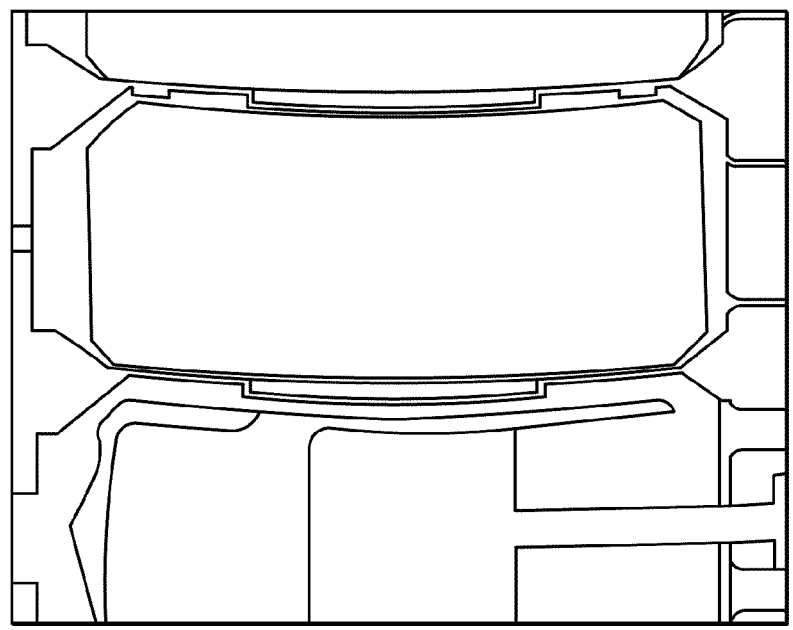
FIG. 5

POLYMER NEMS FOR CELL PHYSIOLOGY AND MICROFABRICATED CELL POSITIONING SYSTEM FOR MICRO-BIOCALORIMETER

CROSS-REFERENCE TO RELATED APPLICATIONS

This application is a divisional application of the following United States patent application, which is incorporated by reference herein:

U.S. patent application Ser. No. 11/830,612, filed on Jul. 30, 2007, for "POLYMER NEMS FOR CELL PHYSIOLOGY AND MICROFABRICATED CELL POSITIONING SYSTEM FOR MICRO-BIOCALORIMETER" by MICHAEL L. ROUKES, CHUNG WAH FON, WONHEE LEE, HONGXING TANG, BLAKE WATERS AXELROD, and JOHN LIANG TAN, which application claims the benefit under 35 U.S.C. Section 119(e) of the following commonly-assigned U.S. provisional patent application(s), which is/are incorporated by reference herein:

Provisional Application Ser. No. 60/834,253, filed on Jul. 28, 2006, by Michael L. Roukes, Chung-Wah Fon, Wonhee Lee, and Hongxing Tang, entitled "Vacuum-insulating polymer-based micro-biocalorimeter integrated with microfluidics";

Provisional Application Ser. No. 60/834,052, filed on Jul. 28, 2006, by Blake W. Axelrod, Michael L. Roukes, and John Tan, entitled "Plastic NEMs for cell physiology"; and Provisional Application Ser. No. 60/834,288, filed on Jul. 28, 2006, by Blake W. Axelrod, Michael L. Roukes, and John Tan, entitled "Microfabricated cell positioning system";

STATEMENT REGARDING FEDERALLY SPONSORED RESEARCH AND DEVELOPMENT

The invention was made with Government support under Grant No. N66001-02-1-8914 awarded by NAVY-SPAWAR Systems Center San Diego, and Grant No. W911NF-04-1-0171 awarded by ARO—US Army Robert Morris Acquisition Center. The Government has certain rights in this invention.

BACKGROUND OF THE INVENTION

1. Field of the Invention

The present invention relates generally to nanoscale electromechanical (NEMs) devices, and in particular, to a method, apparatus, and device for a micro-fluidic embedded polymer NEMs force sensor and vacuum insulated polymer based micro-biocalorimeter integrated with microfluidics.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

The development of microcantilever force sensors has enabled development in the field of atomic force microscopy (AFM). AFMs are important tools in nanoscience and have further led to the development of cantilever based sensing, including a wide range of scanning probe microscopies (SPM), and many different forms of static (that is non-scanned) sensing. SPMs are used to image local forces arising from magnetic and magnetic resonance interactions; forces from local electrostatics, surface potentials, surface temperatures, and chemical bonding; and forces from many other local origins. Similarly, applications for non-scanned microcantilever sensors are equally diverse, including infrared imaging, nanocalorimetry, vapor- and liquid-phase chemisensing, electrometry, mass detection, etc.

However, at microscale dimensions, there are limits with respect to the level of frequency achievable and the level of sensitivity attainable. In this regard, the standard approaches used to make microelectromechanical systems (MEMS) cannot provide access to the nanoscale, where very large improvements in sensitivity can be attained [1]. Recent demonstrations and applications of the unprecedented sensitivity available from nanoelectromechanical (NEMS) devices include milestones such as sub-single-charge electrometry [2], single-electron-spin paramagnetic resonance [3], zeptogram-scale mass sensing [4], zeptonewton-scale force sensing [5] and subfemtometer displacement sensing [6]. In fact, with these continuing advances, NEMS sensors are rapidly converging towards the ultimate, quantum limits of force and displacement detection [7].

However, in contrast to MEMS, NEMS devices are still largely pursued only within the province of specialists. A current barrier to their practical development and widespread use is the difficulty of achieving sensitive displacement transduction at the nanoscale. Beyond the initial challenges of fabricating ultra-small mechanical devices, successful realization of NEMS involves addressing the doubly hard challenge of realizing very high frequency displacement sensing while attaining extreme subnanometer resolution. This is not straightforward; approaches to displacement transduction commonly used for MEMS generally are not applicable to NEMS [8]. For example, the efficiency of capacitive detection precipitously decreases at the nanoscale, and the signal is typically overwhelmed by uncontrollable parasitic effects.

Existing prior art techniques used to measure forces exerted by biological structures have been primarily limited to optical measurements. For optical readouts, diffraction effects become pronounced when device dimensions are scaled far below the wavelength of the illumination used. Furthermore, existing readouts for scanned probe microscopy cantilevers are predominantly based upon external (that is, off-chip) displacement sensing systems that, typically, greatly exceed the size scale of the cantilever sensors themselves. The most common SPM readouts are optically based, involving simple optical beam deflection or more sensitive interferometry. By comparison, only a relatively small subset of efforts has focused upon development of self-sensing nanocantilevers.

In addition to the above, the ability to measure forces exerted by biological specimens have encountered significant limitations. In this regard, prior art techniques have focused on optical measurement techniques. In such an environment, the amount of resolution attainable is limited. Further, prior art techniques fail to provide an efficient mechanism to deliver individual cells to specific force sensors and fail to precisely control the chemical environment around a cell under study. In addition, prior art delivery and control systems fail to maintain the viability of the biological sample under study while providing a mechanism to extract signals from a force sensor to a computer for readout and analysis.

In view of the above, what is needed is a NEMs force sensor for use in biological applications that can be used in an efficient and controlled environment.

In addition to the above, calorimeters are used in the prior art to detect enthalpy change of chemical and biological reactions. However, measurement sensitivity of microfabricated calorimeters/thermometers fail to achieve the measurement sensitivity compatible to that of large scale calorimeters. Such a lack of measurement sensitivity is determined by the sensitivity of the thermometer and capability to maximize the signal with good thermal isolation. However, the prior art has failed to increase sensitivity to minimize the heat loss of the sample. Accordingly, what is needed is a microcalorimeter that is useful in biological applications and that provides sufficient measurement sensitivity.

SUMMARY OF THE INVENTION

One or more embodiments of the invention encompasses a force sensing nanoscale electromechanical (NEMs) device for biological applications, such as the contraction of a cell's lamellipodia. The force sensor is a doubly clamped beam fabricated from a polymer, such as SU-8, with a piezoresistive strain sensor patterned asymmetrically through the beam so as to integrate over the regions of maximum tensile strain. The piezoresistive strain sensor is made from a conductor, such as a metal like gold. The force sensor can be positioned next to a ledge or suspended bridge for supporting a single cell and performing force measurements on cell contraction. If the entire device is mounted on a flexible substrate the force-sensing beam can also be used to exert force back on a cell by flexing the substrate parallel to the beam. Furthermore, the stiffness of the force sensor can be tuned by flexing the substrate perpendicular to the beam.

In addition, one or more embodiments of the invention provide calorimeter capable of detection of enthalpy change of chemical and biological reaction, such as enzyme activity and protein-ligand binding, in a 3.5 nanoliter (nL) volume. The calorimeter is embedded in parylene microfluidic system and can be coupled to other lab-on-a-chip microfluidic devices. Microfabrication of the calorimeter array and the accompanying microfluidic circuitry has enabled rapid and parallel implementation of calorimetric measurement. The reduction in scale also reduces the time and sample quantity required for such measurement. Sophisticated thermal insulation is engineered to maximize the measurement sensitivity. While a batch calorimeter is demonstrated, the calorimeter can be modified to perform isothermal titration, differential scanning and flow calorimetry.

BRIEF DESCRIPTION OF THE DRAWINGS

Referring now to the drawings in which like reference numbers represent corresponding parts throughout:

FIG. 3 illustrates the various dimensions of a beam and strain sensor used in accordance with one or more embodiments of the invention;

FIG. 5 illustrates a polymer strain sensor fabricated in accordance with one or more embodiments of the invention;

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview—Microfluidic Embedded Polymer NEMs Force Sensor

As described above, prior art techniques have attempted to measure the forces exerted by biological samples (e.g., single cells). In this regard, adherence cells (i.e., cells that adhere or have adhering properties with respect to adjacent surfaces), may exert forces when diffused across a surface. Prior art mechanisms attempted to measure such forces primarily utilizing optical means. In this regard, prior art mechanisms were based on optical measurements of deflected substrates or members. For example, cells (e.g., monocyte or macrophage cells), may be placed superior to polydimethylsiloxane (PDMS) (e.g., PDMS pillars/structures) and any resulting deformation in the PDMS structure was optically measured. However, the resolution of such measurements was insufficient. In this regard, prior art mechanisms were insufficient for measuring the displacement/deformation of single cell structures. Further, such optical measurement techniques are expensive and cell delivery and control is difficult.

To overcome the disadvantages of the prior art, one or more embodiments of the invention utilize a microfluidic embedded polymer NEMs force sensor. To more easily understand the invention, a description of the overview of the force sensor and microfluidics are followed with independent descriptions of the force sensor and the microfluidic aspects of the invention.

One or more embodiments of the invention provide a force sensor for biological applications, e.g. measuring forces exerted by a single cell. The force sensor may consist of a doubly clamped beam fabricated from a polymer (e.g., plastic) with a piezo resistive strain sensor patterned asymmetrically through the beam so as to couple to regions of maximum tensile or compressive strain. Beams can be fabricated using the following polymers: SU Polymer family (e.g., SU8 2000, SU-8 3000, etc.) PolyImide, Parylene. The piezo resistive strain sensor can be made from any conductive material (e.g., a metal such as gold with a very thin titanium or chromium adhesion layer).

Figure 1:
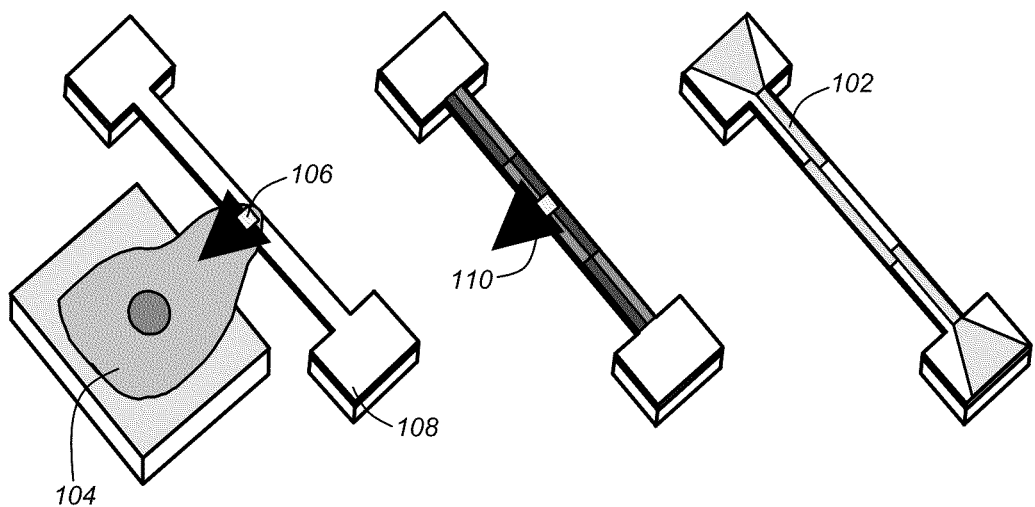
FIG. 1 illustrates a c-shape strain sensor used in accordance with one or more embodiments of the invention.

Beams can been fabricated for measuring in-plane forces by patterning the piezo-resistive strain sensor 102 asymmetrically in the horizontal plane using a c-shape and symmetrically out of the plane by sandwiching the strain sensor 102 between two layers of polymer (e.g., plastic) of the same thickness. FIG. 1 illustrates a c-shape strain sensor 102 in accordance with one or more embodiments of the invention. As illustrated, the piezo-resistive strain sensor 102 is patterned asymmetrically in the horizontal plane of the beam. The pattern is based on those areas of the beam that are likely to stretch or strain as a result biological force exertion. The biological sample 104 is placed with respect to a defined location 106 of the beam 108 and the strain of the piezo-resistive strain sensor 102 is able to measure the in-plane forces/displacement (indicated by arrow 110) of the beam caused by the introduction of the biological sample 104.

Figure 2:
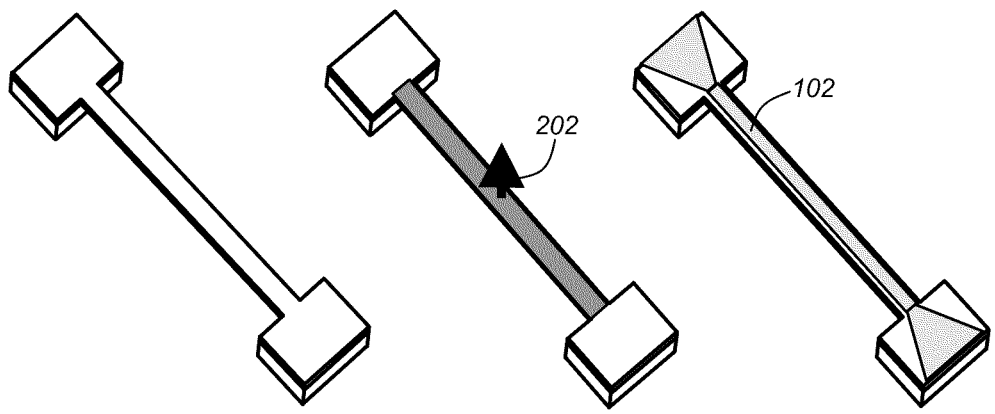
FIG. 2 illustrates a straight-line strain sensor in accordance with one or more embodiments of the invention.

Beams have also been fabricated for measuring to out-of-plane forces by patterning the piezo-resistive strain sensor 102 symmetrically in the horizontal plane using a straight line pattern and asymmetrically out of the plane by placing the strain sensor 102 on top of or on the bottom of the polymer/plastic layers or by sandwiching the strain sensor 102 between two layers of polymer/plastic of different thickness. FIG. 2 illustrates a straight-line strain sensor in accordance with one or more embodiments of the invention. As illustrated in FIG. 2, the strain sensor 102 is fabricated in a straight-line pattern to measure out-of-plane forces indicated by arrow 202.

For applications in fluid, particularly buffered solutions used in biological applications, it is advantageous to sandwich the strain sensor 102 between two layers of polymer (e.g., plastic) in order to electrically isolate the strain sensor 102 from the fluid. Such isolation insulates the force/strain sensor 102 and isolates the sensor 102 from any conductivity present in the buffered solution/fluid.

The force sensors can be encapsulated in PDMS (polydimethylsiloxane) microfluidics for use in fluid. Multi-layer microfluidics with control valves may be mounted on the front side of the chip with the force sensor. A glass cover slip can also be mounted on the backside of the chip and sealed with a thin layer of PDMS. The glass cover slip enables high resolution microscopy simultaneously with use of the force sensor.

Polymer NEMs Force Sensor

Described below is a detailed description of the force sensor used in accordance with embodiments of the invention.

Various symbols may be used in the description that follows. The following presents a list of such symbols and their intended meaning $\alpha$—material dependent hooge parameter
E—Young's modulus
$\epsilon$—strain
F—force
f—frequency
$\zeta$—thickness of piezoresistive wire
G—tension force
I—moment of intertia
K—spring constant
$k_B$—Boltzmann's constant
$\kappa$—transducer responsivity
l—substrate length
L—length of beam
$\lambda$—filter setting
N—number of carriers
n—carrier density
$\pi_1$—longitudinal piezoresistance coefficient
R—resistance
$\delta R$—change in resistance
r(x)—radius of curvature
$\vec{r}$—cartesian vector
$\vec{\rho}$—cartesian vector
$\rho$—resistivity
$S_{Th}$—thermal noise voltage spectral density
$S_H$—hooge noise voltage spectral density
$\sigma_0$—surface stress distribution
T—substrate thickness
t—thickness of beam
$\tau$—time constant
$V_0$—input voltage
$\delta V$—voltage signal
$\upsilon$—poison ratio, width of piezoresistive wire
w—width of beam x—x-coordinate
y—y-coordinate
ΔX(r)—displacement of surface at r in x direction
ΔY(x)—displaimenet of centerline of beam in y direction
δz—vertical displacement I. Device: Clamped Beam with Piezoresistive Strain Gauge a. Beam Displacement and Spring Constant The displacement of the center line of a doubly clamped beam due to a force exerted at the beam's mid point is given by:

$$\Delta Y(x) = F \frac{x^2(3L - 4x)}{4Etw^3}, \quad (1)$$

where x extends from zero to L/2, t, w, and L are the thickness, width and length of the beam as shown in FIG. 3, E is the young's modulus and F is the applied force [P1]. Accordingly, FIG. 3 illustrates the various dimensions of a beam and strain sensor used in accordance with one or more embodiments of the invention.

The effective spring constant, K, is defined by the displacement at the midpoint, x=L/2:

$$K = \frac{F}{\Delta Y(x = L/2)} = \frac{16Etw^3}{L^3}. \quad (2)$$

Equation (2) has been checked with CFDRC and agrees within half of one percent. Table 1 (below) lists in plane (ky) and out of plane (kz) spring constants for a few relevant geometries and material properties. Two things of note, first the smallest silicon beams are roughly a factor of 30 stiffer than the smallest Su8 beams, second the Su8 beams are roughly a factor of 50 stiffer than the gold beams which can be patterned inside of them.

b. Strain in Piezoresistor

A strain gauge is integrated into the beam by patterning a u-shaped piezoresistive (PZR) conductor of width υ and thickness ζ symmetrically across the four quarters of the beam, shown FIG. 3. The u-shaped pattern will maximize the strain induced by the displacement described in eq (1). The strain in an infinitesimal element of the PZR conductor at x,y is given by [P1]:

$$\varepsilon = \frac{y}{r(x)}, \quad (3)$$

where y is the displacement in the ŷ direction from the center line of the beam and r is the radius of curvature of the center line at that point. One can approximate the radius of curvature:

$$\frac{1}{r(x)} = \frac{d^2}{dx^2} \Delta Y(x) = F \frac{6L - 24x}{4Etw^3}. \quad (4)$$

Each quarter of the piezoresistor will be symmetric with strain, thus one need only integrate over one quarter of the wire to determine the average strain:

$$\bar{\varepsilon} = \frac{1}{\text{area}} \int \frac{y}{r(x)} d(\text{area}) = \frac{F}{(\upsilon)(L/4)} \int_{w/2-\upsilon}^{w/2} \int_0^{L/4} \frac{y(6L - 24x)}{4Etw^3} dx\, dy, \quad (5)$$

which is easily integrated:

$$\bar{\varepsilon} = \frac{3}{8} \frac{F}{E} \frac{L(w - \upsilon)}{tw^3}. \quad (6)$$

Equation (6) has also been checked with CFDRC and agrees within 1%.

c. Wheatstone Bridge and Transducer Responsivity

The strain gauge will use the piezoresistance effect to convert the induced strain, eq (6), into a change in resistance:

$$\frac{\delta R}{R} = \pi_l \bar{\varepsilon} = \frac{3}{8} \frac{\pi_l}{E} \frac{L(w - \upsilon)}{tw^3} F, \quad (7)$$

where $\pi_l$ is the piezoresistance coefficient for the wire. For the silicon in the BioNEMs chips, one expects a $\pi_l$ of 40 and roughly 47 have been measured for the transducer responsivity with the AFM. For gold, geometric considerations predict a $\pi_l$ of 2 for bulk metals, but Thaysen et. al. [P2] report a value of roughly 4; the discrepancy is possibly due to thin film effects.

The force sensing beam may be integrated into an on chip Wheatstone bridge with one suspended reference beam and two supported balance resistors. When optimally balanced the Wheatstone bridge converts a change in resistance into a voltage signal according to:

$$\delta V = V_0 \frac{1}{4} \frac{\delta R}{R}, \quad (8)$$

where $V_0$ is the voltage applied to the bridge. Combining equations (7) and (8) one obtains the proportionality constant between the applied force and the measured voltage signal—the transducer responsivity, κ, of the force sensing beam:

$$\delta V = \frac{3}{32} \frac{\pi_l}{E} \frac{L(w - \upsilon)}{tw^3} V_0 F = \kappa F, \quad (9)$$

$$\kappa = \frac{3}{32} \frac{\pi_l}{E} \frac{L(w - \upsilon)}{tw^3} V_0 \quad (10)$$

d. Electrical Noise

There will be four electrical contributions to the noise: amplifier voltage noise $e_n$, amplifier current noise $i_n$, Johnson noise, and 1/f noise. The voltage spectral density of Johnson noise is frequency independent:

$$S_{Th} = 4k_B T R = \frac{4k_B T \rho L}{\zeta \upsilon}, \quad (11)$$

where the second equality comes from the geometric dependence of the resistance. The amplifier voltage and current noise spectral densities, $e_n^2$ and $i_n^2$, are also frequency independent. Hooge noise, or 1/f-noise, is named after its' frequency dependence:

$$S_H = \frac{\alpha V^2}{fN} = \frac{\alpha V^2}{fn\zeta vL}, \quad (12)$$

where $\alpha$ is material dependent, N is the number of carriers and n is the density of carriers. The noise voltage power is determined by integrating the spectral density over the measurement frequency range:

$$\langle V_{Noise}^2 \rangle = (f_{max} - f_{min}) \left( \frac{4k_B T \rho L}{\zeta v} + e_n^2 + \left( \frac{i_n \rho L}{2\zeta v} \right)^2 \right) + \frac{\alpha V^2}{n\zeta vL} \ln\left[ \frac{f_{max}}{f_{min}} \right] \quad (13)$$

The force noise is determined by combing equations (9) and (13):

$$F_{Noise}^2 = \left( \frac{32}{3} \frac{E}{\pi_l} \frac{1}{V_0} \frac{tw^3}{L(w-v)} \right)^2 \quad (14)$$

$$\left( (f_{max} - f_{min}) \left( \frac{4k_B T \rho L}{\zeta v} + e_n^2 + \left( \frac{i_n \rho L}{2\zeta v} \right)^2 \right) + \frac{\alpha V^2}{n\zeta vL} \ln\left[ \frac{f_{max}}{f_{min}} \right] \right).$$

The bandwidth, $f_{min}$, and $f_{max}$, is determined by the lock-in amplifier used, in particular the source frequency f, the time constant $\Sigma$, and the low pass filter roll-off. For the following I assume a SRS 830 lock-in with source frequency of 100 kHz, a minimum time-constant of 10 μs and low pass filter settings of 6 db/oct, 12 db/oct, 18 db/oct or 24 db/oct. The time resolution δ will be determined by the time constant and low pass filter settings, Table 2 summarizes the relationship between these three variables.

TABLE 2

| Equivalent noise bandwidth ($f_{max} - f_{min}$) | Time resolution, δ |
|---|---|
| ¼τ = ⁵/₄δ = λδ | 5τ |
| ⅛τ = ⁷/₈δ = λδ | 7τ |
| ³/₃₂τ = ²⁷/₃₂δ = λδ | 9τ |
| ⁵/₆₄τ = ⁵⁰/₆₄δ = λδ | 10τ |

For a given filter setting, λ, and source frequency, f, one can determine the force noise and thus force resolution as a function of the time resolution):

$$F_{Noise} = \left( \frac{32}{3} \frac{E}{\pi_l} \frac{1}{V_0} \frac{tw^3}{L(w-v)} \right) * \quad (15)$$

$$\sqrt{ \left( \frac{\lambda}{\delta} \left( \frac{4k_B T \rho L}{\zeta v} + e_n^2 + \left( \frac{i_n \rho L}{2\zeta v} \right)^2 \right) + \frac{\alpha V^2}{n\zeta vL} \ln\left[ \frac{f + \lambda/2\delta}{f - \lambda/2\delta} \right] \right) }.$$

One may apply the noise analysis embodied in eq. (15) and table (2) with the appropriate optimized bandwidth and filter settings for an SRS 560 pre-amp and SRS 830 lock-in amplifier to the 36 different combinations of materials, beam dimensions and PZR strain gauge dimensions listed in table (3).

Figure 4A:
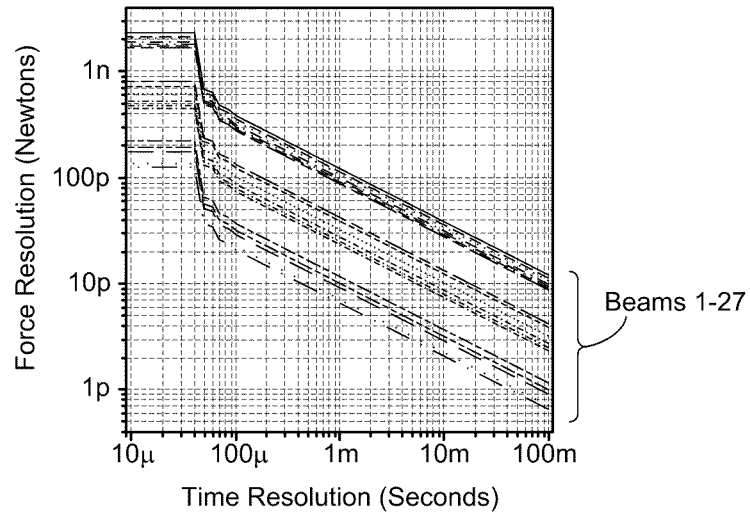
FIG. 4A illustrates the estimated force resolution for SU-8 beams in accordance with one or more embodiments of the invention.
Figure 4B:
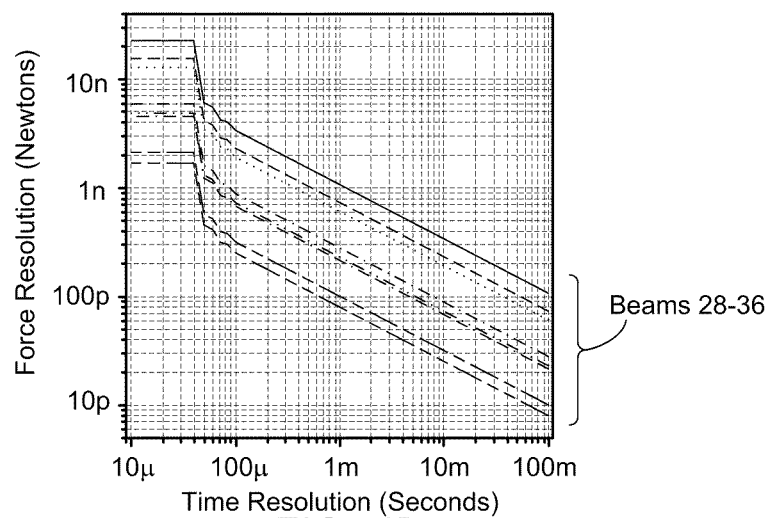
FIG. 4B compares SU-8 and silicon beams in accordance with one or more embodiments of the invention.

The principle piece missing from this analysis is an optimization of the input voltage applied to the Wheatstone bridge. Fluidic noise, which will be discussed in the following section is also missing from this analysis, but is expected to be negligible. The estimated force resolution for the Su8 beams is plotted in FIG. 4A, for the silicon beams identified in the inset of FIG. 4A. FIG. 4B compares the Su8 and silicon beams.

The results of this noise analysis indicate that beams #20 & 21, made of Su8 with length 100 μm, width 1 μm, thickness 400 nm, PZR thickness 50 nm and PZR widths 200 nm and 100 nm respectively, yield the best force and time resolution: 120 pN at 10 μs, 20 pN at 100 μs and 6.5 pN at 1 ms. The best silicon beams, by comparison, are #34 & 35 which offer force resolution of 2 nN at 10 μs, 280 pN at 100 μs and 80 pN at 1 ms; roughly a factor of 15 worse than the best Su8 beams.

The dynamic range of this measurement can be determined by the onset of non-linearity within the beam.

e. Demonstration of Strain Sensor

Polymer (e.g., plastic) strain sensors (as described above) have been successfully fabricated with a length of 100 microns, a width of 4 microns, a thickness of 530 nm and with a gold piezoresistive strain gauge that is 500 nm wide and 40 nm thick. FIG. 5 illustrates a polymer strain sensor fabricated in accordance with one or more embodiments of the invention.

Figure 6A:
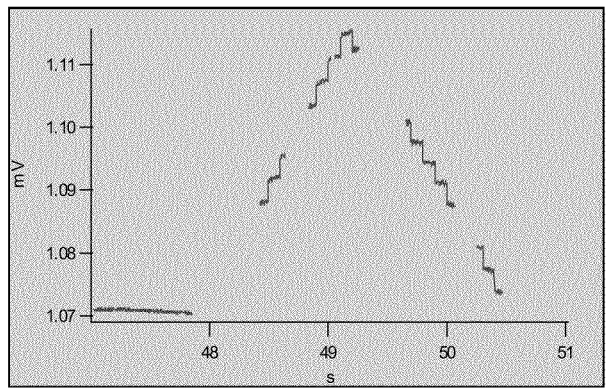
FIG. 6A shows the response of the beam to a stepwise increase and decrease in applied force in accordance with one or more embodiments of the invention.
Figure 6B:
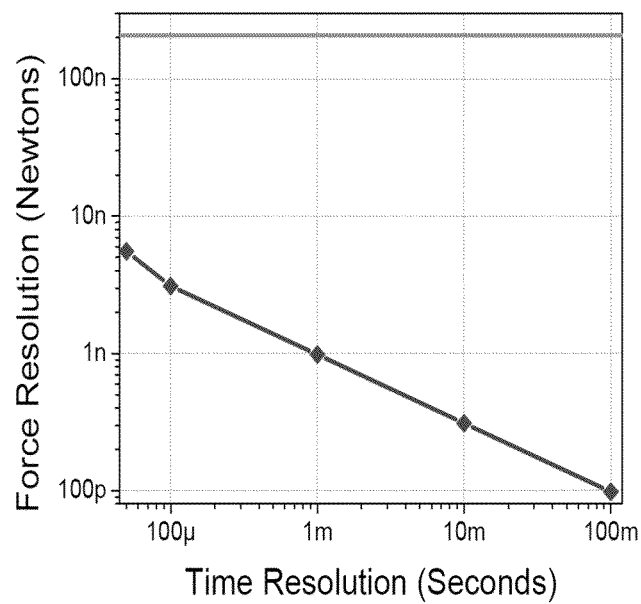
FIG. 6B shows the force sensitivity as a function of time resolution for a beam in accordance with one or more embodiments of the invention.

The device of FIG. 5 has been calibrated using a glass micro needle. The transducer responsivity is 65 V/N at a drive voltage of 0.5 Vrms. FIG. 6A shows the response of the beam to a stepwise increase and decrease in applied force. FIG. 6B shows the force sensitivity as a function of time resolution for this beam.

f. Force Application by Device

Figure 7:
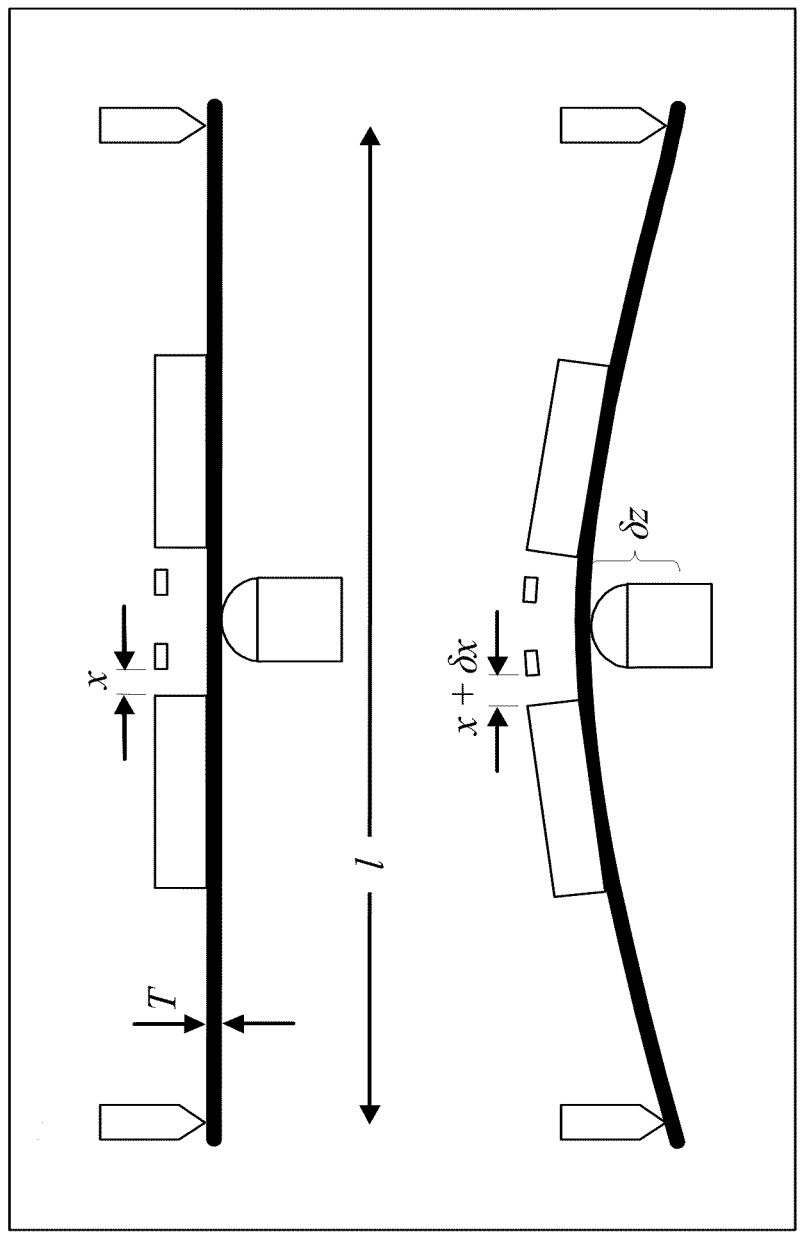
FIG. 7 illustrates how the distance between the beam and the ledge can be increased by bending the substrate in accordance with one or more embodiments of the invention.

The plastic, SU-8, beams may be attached to a flexible substrate and then by bending the substrate it is possible to either change the distance between the beam and the ledge or to apply a tension to the beam, depending on whether the bending axis is parallel or perpendicular to the beam. FIG. 7 illustrates how the distance between the beam and the ledge can be increased by bending the substrate in accordance with one or more embodiments of the invention. As illustrated, the top portion of FIG. 7 illustrates the beam without any bending of the substrate (and a distance of x). Once the substrate is bent, as illustrated in the bottom portion of FIG. 7, the distance between the beam and the ledge increases (i.e., x+δx).

Application of equation (3) to the geometry in FIG. 7 gives the displacement, δx, in terms of the curvature of the substrate:

$$\frac{\delta x}{x} = \frac{(T/2)}{r}, \quad (23)$$

where one may assume that the neutral plane of the deflection is in the middle of the flexible substrate. If the radius of curvature is sufficiently large, r>>1, then it can be expressed in terms of δz:

$$\frac{1}{r} = \frac{6\delta z}{l^2}. \quad (24)$$

Figure 8:
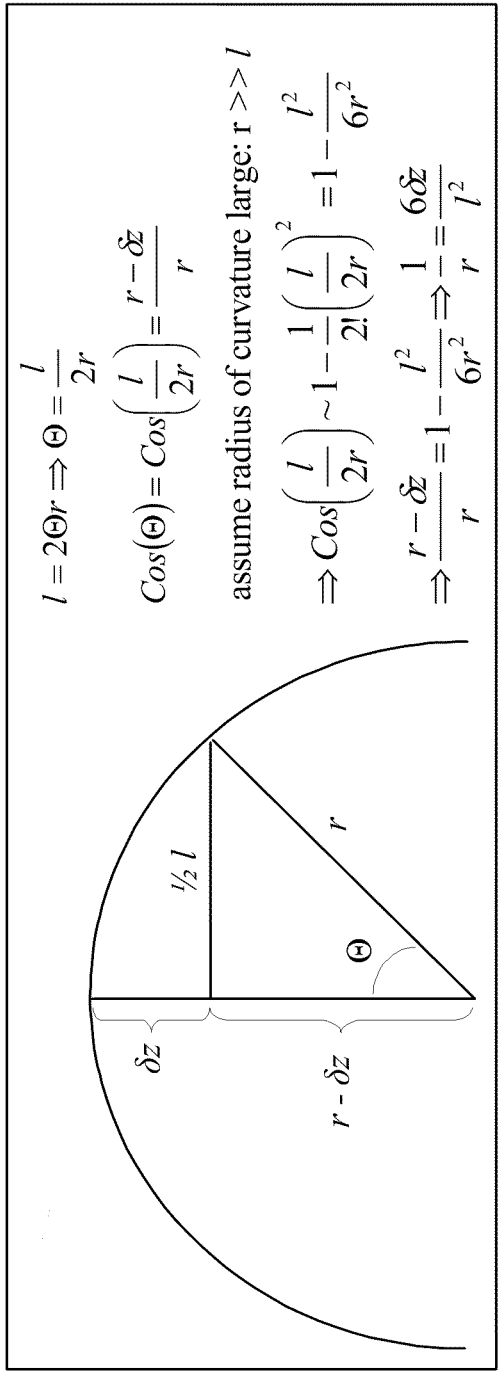
FIG. 8 illustrates a derivation of an equation for the radius of curvature in accordance with one or more embodiments of the invention.

The derivation of equation (24) is shown in FIG. 8.

By combining equations (23) and (24) one obtains the displacement in terms of the vertical displacement, δz, which is the relevant experimental variable:

$$\delta x = \frac{3Tx}{l^2}\delta z. \quad (25)$$

This result differs from a similar derivation by Ruitenbeek et. al. [P23] by a factor of 2 in which the neutral surface is assumed to be at the bottom surface of the flexible substrate.

Figure 9:
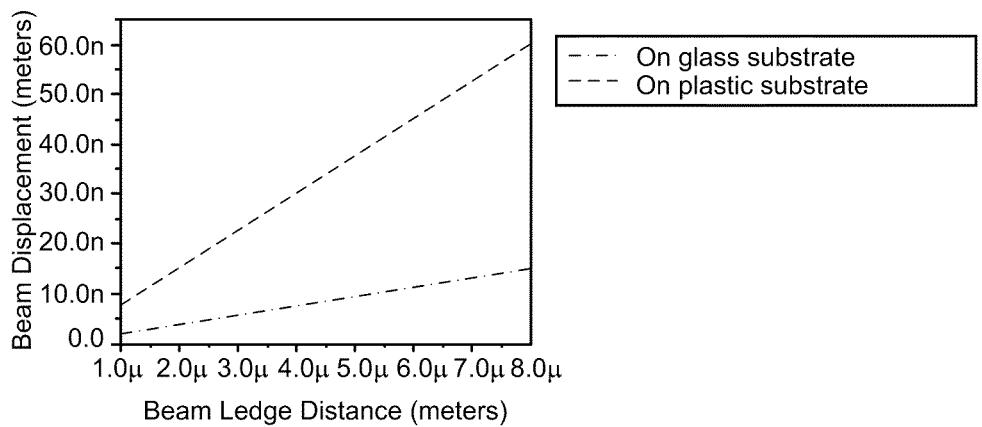
FIG. 9 shows the maximum beam displacement as a function of the beam to ledge separation, which must be kept small enough to allow a cell's lamelipodia to span the gap in accordance with one or more embodiments of the invention.

In the experimental setup described herein, the vertical displacement may be controlled by a piezoelectric stage such as a long-travel piezo flexure stage (e.g., part number P-290 available from Physik Instrumente (PI) GmbH & Co. KG) which has a maximum travel of 1000 μm and an open-loop displacement resolution of 20 nm. The displacement resolution is limited by the voltage noise of the amplifier used to drive the piezoelectric stage. Potential substrates include number 1 cover glass (T=250 μm) or stiff plastic (T=1000 μm)—cover glass will enable high resolution microscopy, whereas the plastic will enable greater force application. A substrate width, l, of 2 cm is necessary to enable electronic and fluidic integration/fanout. FIG. 9 shows the maximum beam displacement as a function of the beam to ledge separation, which must be kept small enough to allow a cells lamelipodia to span the gap.

The force exerted on the cell by displacing the beam as described above will depend on the spring constant of the beam, given by equation (2), and Hook's law:

$$F = K\delta x = \left(\frac{16Etw^3}{L^3}\right)\left(\frac{3Tx}{l^2}\right)\delta z w^3 \ldots \quad (26)$$

Figure 10A:
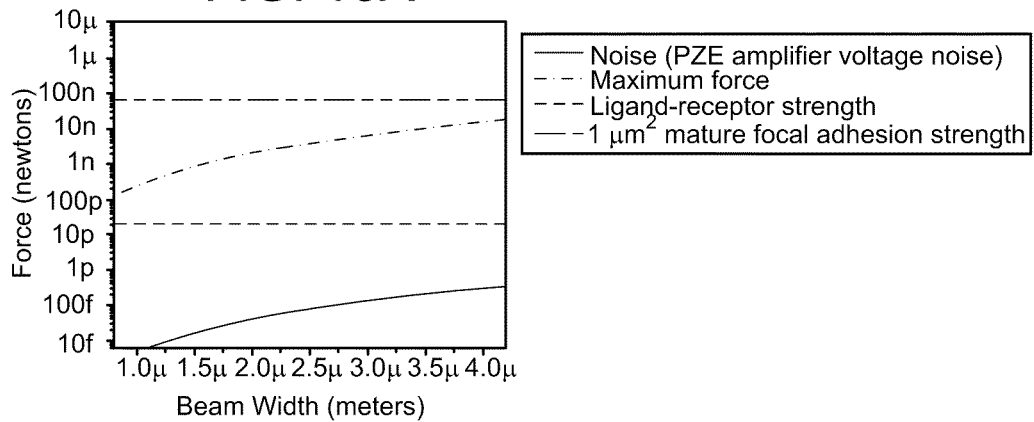
FIG. 10A illustrates a force application with a glass substrate and FIG. 10B illustrates a force application with a plastic substrate in accordance with one or more embodiments of the invention.
Figure 10B:
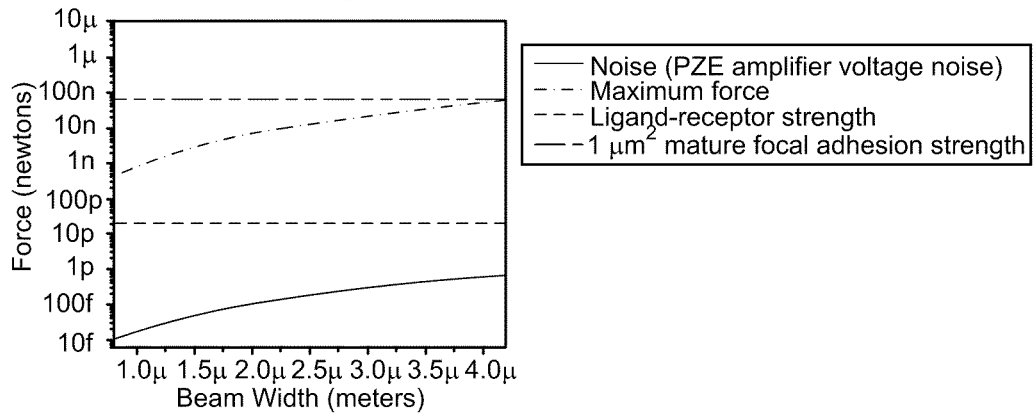

FIGS. 10A and 10B show the force resolution and maximum force that can be applied by the beams analyzed in section (d) above as a function of beam width for a cover glass substrate and a plastic substrate with a beam to ledge separation of 4 μm. In this regard, FIG. 10A illustrates a force application with a glass substrate and FIG. 10B illustrates a force application with a plastic substrate in accordance with one or more embodiments of the invention.

g. Device Stiffening: Tuning the Spring Constant

The previous section detailed how bending of the substrate can be used to move the beam with respect to the ledge and thus exert a force on the cell under study. The same principle can be used to apply a tension to the beam that will increase the beam's effective spring constant by bending the substrate around an axis perpendicular to the beam. Replacing the beam to ledge distance, x, in equation (25) with the length of the beam, L, one obtains an expression for the change in length of the beam as a function of the vertical extension, δz:

$$\delta L = \frac{3TL}{l^2}\delta z. \quad (27)$$

The tension induced from this extension of the beam is:

$$G = Etw\frac{\delta L}{L} = \frac{3ETtw}{l^2}\delta z. \quad (28)$$

The displacement of the center line of a doubly clamped beam under tension force, G, due to a force, F, exerted at the beam's mid point is given by:

$$\Delta Y(x) = \frac{F}{2G}\left(x - \frac{1}{k}\mathrm{Sinh}(kx) + \frac{\mathrm{Cosh}\left(\frac{kL}{2}\right)-1}{k\mathrm{Sinh}\left(\frac{kL}{2}\right)}(\mathrm{Cosh}(kx)-1)\right), \quad (29)$$

$$k = \sqrt{\frac{G}{EI}} = \sqrt{\frac{12G}{Etw^3}} = \frac{6\sqrt{T\delta z}}{wl}.$$

Similar to the analysis in section (a) of the beam without tension, one can define the effective spring constant, K, by the displacement at the midpoint, x=L/2:

$$K = \frac{F}{\Delta Y(x=L/2)} \quad (30)$$

$$= \frac{36Etw(T\delta z)^{3/2}}{3Ll^2\sqrt{T\delta z} - (wl^3)\mathrm{Sinh}\left(\frac{3L\sqrt{T\delta x}}{wL}\right) +} \cdot$$

$$(wl^3)\frac{\left(\mathrm{Cosh}\left(\frac{3L\sqrt{T\delta z}}{wL}\right)-1\right)^2}{\mathrm{Sinh}\left(\frac{3L\sqrt{T\delta z}}{wL}\right)}$$

Equation (30) may be simplified with the observation that $wl^3 \ll 3 L l^2\sqrt{(T\delta z)}$:

$$K = \frac{12EtwT\delta z}{Ll^2} \quad (31)$$

which, is clearly not correct because the spring constant in equation (31) goes to zero when the vertical displacement goes to zero, but the spring constant should revert to equation (2). If one views the above as a calculation of the change in spring constant due to the vertical displacement, then, the total spring constant would be the sum of equations (2) and (31):

$$K = \frac{16Etw^3}{L^3} + \frac{12EtwT\delta z}{Ll^2} = \frac{4Etw}{L}\left(\frac{4w^2}{L^2} + \frac{3T\delta z}{l^2}\right), \quad (31)$$

Figure 11:
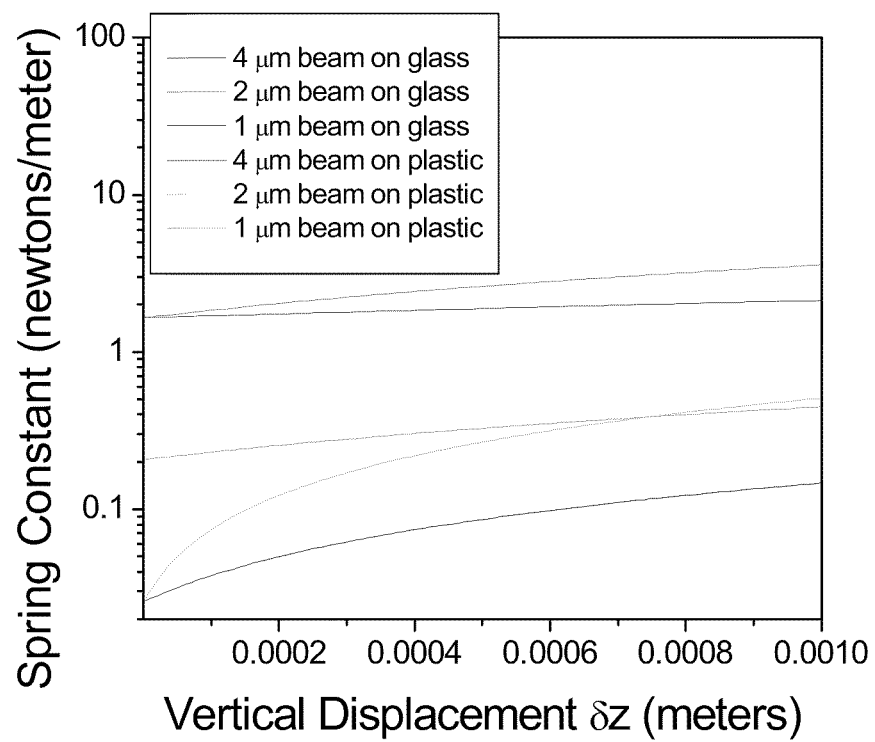
FIG. 11 illustrates the tuning of a spring constant in accordance with one or more embodiments of the invention.

A plot of the spring constant as a function of the vertical displacement for the beams discussed in section (d) and the substrates discussed in section (f) is shown in FIG. 11. Accordingly, FIG. 11 shows that the change in spring constant for the wide beams (4 μm) is negligible, but for the thin beams (1 μm) the spring constant increases by a factor of 5 on the glass substrate and 20 on the plastic.

II. Device Fabrication

Prior art techniques describe optically patterning SU-8 cantilevers and metal wires to use as piezo-resistive strain sensors (e.g., deformable members), made from polymers, with transducers for converting deformation into an electrical signal. Additionally, the prior art describes a sacrificial chrome release layer and SU-8 plastic chip that were used in early versions of plastic NEMS, but not in more recent versions (see Thaysen [P2]). However, the prior art cantilevers are intended for use in Atomic Force Microscopes (AFM) and are not embedded in microfluidics. In addition, the prior art utilizes a polymer layer as a "handle" or substrate.

In view of the above, prior art techniques for force measurements were primarily obtained based on optical measurements of deflected substrates or members. Further, prior art techniques do not utilize microfluidics. For example, some prior art techniques utilize soft substrates embedded with fluorescent beads, optical detection of deformation of substrate by cell, an optical readout, heavy computation requirements to extract probabilistic force maps, limited force resolution due to optical readout, limited time resolution due to optical readout & substrate stiffness, and very limited throughput due to computation requirements (see Lo [P18]).

Further, Tan [P19] describes soft posts marked with fluorescent dye, optical detection of deformation of posts by cell, optical readout, limited force resolution due to optical readout, and limited time resolution due to optical readout & substrate stiffness.

One or more embodiments of the present invention overcome the disadvantages of the prior art. In this regard, embodiments of the present invention utilize electrical detection of the deformation, electrical readout, and micro-fluidics. Further, embodiments may utilize stand alone chips as force sensors, may embed force sensors in the micro-fluidics and utilize the force sensors for/in biological applications. In addition, while early designs of the invention may have used an all polymer method, embodiments of the present invention may build polymer force sensors on top of a silicon wafer with openings through the wafer to suspend the force sensors. Also, MPTS adhesion promoters may be utilized. Further, embodiments may use a hot, dilute hydrofluoric acid to selectively etch silicon-nitride in the presence of the polymer force sensors. Such differences between embodiments of the present invention and the prior art may be better understood with a detailed explanation of the fabrication techniques that may be utilized.

The force sensors can be fabricated using an all SU-8 process that produces a finished chip which is all plastic and thus flexible. The fabrication steps for this process are as follows:

1. Deposition of a sacrificial chrome layer onto a silicon wafer. Typically a Ti/Au layer is included below the chrome to aid in the removal of the chrome.

2. Deposition of the first polymer layer for the force sensor. The polymer can be any polymer in the SU-8 polymer family (e.g., SU-8 2000 or SU-8 3000). The polymer layer can be patterned using a direct write of ebeam lithography or photolithography—typically a combination of both is used. Or the layer can remain unpatterned until later—see step 6.

3. Deposition of the metal wire that makes up the piezo-resistive element of the strain sensor. The wire is patterned in PMMA (polymethyl methacrylate) using electron-beam lithography and deposited using electron-beam or thermal evaporation and lift-off in solvent—acetone, tricholorethylene. Typically gold is used as the metal with a thin titanium or chromium adhesion layer. A spin-on organic titanate (AP300) is used to aid adhesion to the polymer layer.

4. Deposition of the second polymer layer for the force sensor. SU-8 2000 or SU-8 3000. The polymer layer can be patterned using a direct write of ebeam lithography or photolithography—typically a combination of both is used. Or the layer can remain unpatterned.

5. Optional patterning and deposition of a metal layer for controlling cell adhesion to the force sensor by creating differences in hydrophobicity between this metal layer and the surrounding polymer or by utilizing surface chemistry differences between the metal layer and surrounding polymer. Patterned in PMMA using electron-beam lithography and deposited using electron-beam or thermal evaporation and lift-off in solvent—acetone, tricholorethylene. Typically gold is used as the metal with a thin titanium or chromium adhesion layer. A spin-on organic titanate (AP300) is used to aid adhesion to the polymer layer.

6. Optional patterning of the polymer layers if they were not directly patterned using lithography in steps 2 & 4. The polymer layers are patterned using an oxygen based plasma etch with a mask to protect the regions which are to remain as structural elements on the force sensor. Typically a metal such as chrome or titanium is used as the etch mask and patterned using electron-beam lithography in PMMA. Electron-beam sensitive polymers such as PMMA and UVN-30 have also been used as etch masks.

7. Patterning and deposition of metal layer for fan-out. A thick metal layer, typically gold with a thin titanium or chrome adhesion layer, is patterned using a bi-layer resist, photolithography and lift-off. Typically 500-1000 nm of metal is necessary to protect wires from breaking when chip flexes.

8. Deposition and patterning of thick polymer layer that will make up the structural support layer of the final chip. Typically 60-80 microns thick SU-8 2000 or SU-8 3000. Vias are patterned with photolithography so that the force sensors will be suspended over openings in the thick polymer layer. It is important that this layer have very low internal stress, low baking temperatures and long baking times are used to achieve low stress.

9. Release of the polymer chip from the silicon wafer by wet etching the sacrificial chrome layer. Best results are achieved by drying the released chips using a critical point drier.

The force sensors can also be fabricated using a silicon-nitride coated silicon wafer as a substrate. This process results in a rigid finished chip, but gives much higher yields. The fabrication steps for this process are as follows:

1. Optional patterning and deposition of a metal layer for controlling cell adhesion to the force sensor by creating differences in hydrophobicity between this metal layer and the surrounding polymer or by utilizing surface chemistry differences between the metal layer and surrounding polymer. Patterned in PMMA using electron-beam lithography and deposited using electron-beam or thermal evaporation and lift-off in solvent—acetone, tricholorethylene. Gold is used as the metal with an organic mercapto-silane monolayer as an adhesion layer. The organic adhesion layer is deposited from an aqueous solution after developing the PMMA and prior to evaporating the metal 2. Deposition of the first polymer layer for the force sensor. SU-8 2000, SU-8 3000, Poly-Imide or parylene can be used. Typically the layer is left unpatterned. However, the SU-8 resists can be directly patterned using electron-beam or photo lithography at this stage.

3. Deposition of the metal wire that makes up the piezo-resistive element of the strain sensor. The wire is patterned in PMMA using electron-beam lithography and deposited using electron-beam or thermal evaporation and lift-off in solvent—acetone, tricholorethylene. Typically gold is used as the metal with a thin titanium or chromium adhesion layer. A spin-on organic titanate (AP300) is used to aid adhesion to the polymer layer.

4. Deposition of the second polymer layer for the force sensor. SU-8 2000, SU-8 3000, Poly-Imide or parylene can be used. Typically the layer is left unpatterned. However, the SU-8 resists can be directly patterned using electron-beam or photo lithography at this stage.

5. Optional patterning of the polymer layers if they were not directly patterned using lithography in steps 2 & 4. The polymer layers are patterned using an oxygen based plasma etch with a mask to protect the regions which are to remain as structural elements on the force sensor. Typically a metal such as chrome or titanium is used as the etch mask and patterned using electron-beam lithography in PMMA. Electron-beam sensitive polymers such as PMMA and UVN-30 have also been used as etch masks.

6. Patterning and deposition of metal layer for fan-out. A thick metal layer, typically gold with a thin titanium or chrome adhesion layer, is patterned using a bi-layer resist, photolithography and lift-off. Typically 200-300 nm of metal is used.

7. Through wafer silicon etch to open vias below the device regions. The backside of the wafer is patterned using photolithography and a window is opened in the silicon-nitride layer using a fluorine based plasma etch. A hot KOH etch is used to etch holes through the silicon wafer leaving only silicon nitride membranes beneath the plastic force sensors.

9. The plastic force sensors are released by preferentially etching the silicon-nitride membrane without damaging the plastic beams. A fluorine based plasma is used to thin the membrane from the back side of the wafer. The membrane removal is finished using a hot, dilute hydrofluoric acid bath which etches silicon nitride without damaging the plastic and metal that comprise the force sensor. After the silicon-nitride membrane has been removed the devices are dried using a critical point drier.

Figure 12:
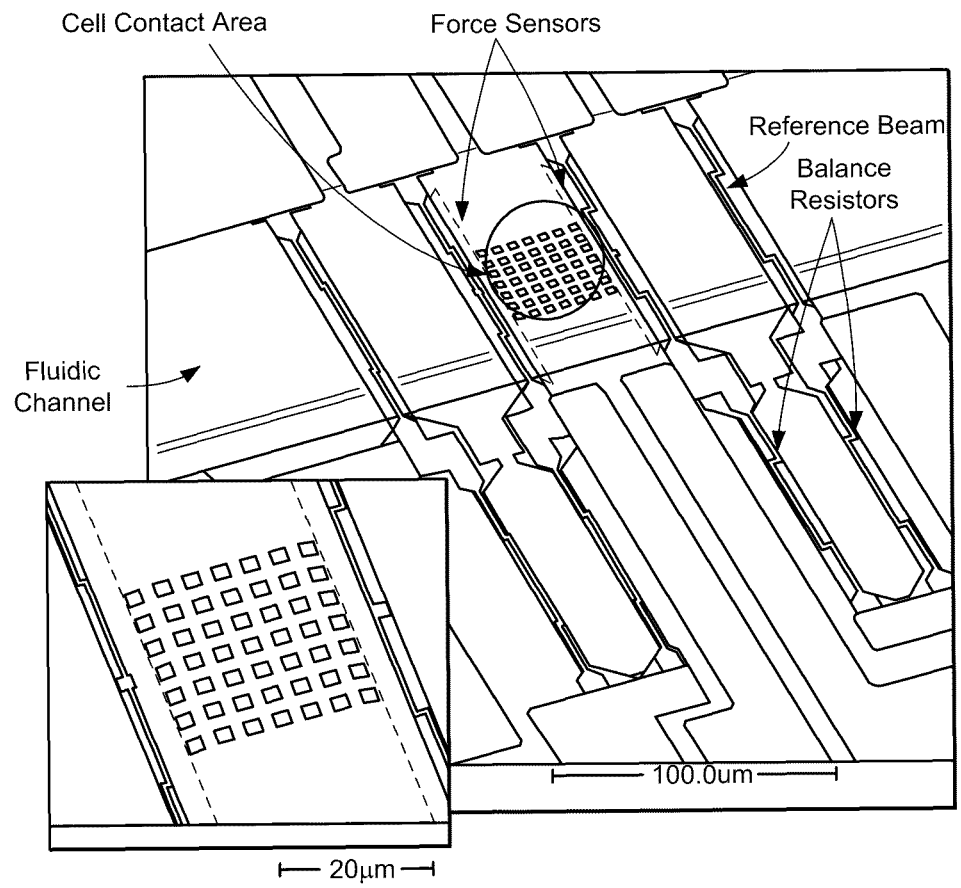
FIG. 12 illustrates an image of a force sensor in accordance with one or more embodiments of the invention.

In view of the above described fabrication techniques, FIG. 12 illustrates an image of a force sensor in accordance with one or more embodiments of the invention. The image is a Scanning Electron Microscope (SEM) image of two force sensors adjacent to a single cell contact area before encapsulation in micro-fluidics. Each force sensor consists of a deformable member and a transducer for reading out the member's deformation electronically.

In FIG. 12, the deformable member is a doubly-clamped beam made from two layers of SU-8 polymer and the transducer is a gold wire sandwiched between the polymer layers and patterned asymmetrically in the horizontal plane using a c-shape. The transducer converts deformations of the beam into electrical signals by the piezo-resistive effect, described in Roukes [P3]. Each force sensor is part of a Wheatstone bridge that includes two balance resistors and one reference beam in addition to the force sensor.

The force sensors have been fabricated on a silicon-nitride coated silicon wafer and suspended over an opening etched in the wafer. This opening makes up part of the fluidic channel that surrounds the force sensor. The rest of the fluidic channel is made from silicone rubber (Poly-DiMethyl-Siloxane or PDMS) based micro-fluidics that are not shown in this image.

The force sensors have been suspended from the wafer's surface by etching a hole through the wafer from the backside using a potassium hydroxide etch to remove the silicon and a combination of a fluorine based plasma etch and a hot, dilute hydrofluoric acid etch to remove the silicon-nitride layer.

The hot, dilute hydrofluoric acid etch is important because it selectively and specifically etches the silicon-nitride without damaging the polymer and metal that comprise the force sensor. The use of hot, dilute hydrofluoric acid to etch silicon-nitride is described in Knotter [P4] which focuses on selecting the etching of silicon-nitride over silicon-dioxide in CMOS process. Accordingly, embodiments of the invention provide for the use of hot, dilute hydrofluoric acid to etch silicon-nitride for the purpose of suspending polymer structures without damaging those polymer.

In the particular instance of a force sensor for measuring forces from a cell, the hot, dilute hydrofluoric acid etch serves a second purpose: the hydrofluoric acid leaves the polymer surface hydrophobic and exposed gold regions hydrophilic. The hydrophobic and hydrophilic nature of these surfaces is critical for the surface chemistry techniques described below.

In the particular instance of a force sensor for measuring forces from a cell with cell contact pads using a titanium adhesion layer, the hot, dilute hydrofluoric acid etch serves a third purpose: the hydrofluoric acid selectively removes the titanium adhesion layer to expose the gold pad without damaging the gold surface. Removal of the titanium adhesion layer is critical to the surface chemistry techniques described below.

In addition to the above, the force sensors may be intended for use measuring forces exerted by individual adherent cells on their surroundings. This requires a cell contact area in close proximity to the force sensors. The cell contact area is a relatively rigid area adjacent to the force sensor upon which an adherent cell can make contact and spread. In one or more embodiments, the cell contact area is defined by a grid of metal (gold) squares. The gold squares can be used to control where the cell attaches utilizing the surface chemistry techniques. Similar gold squares have been patterned on each force sensor in order to control the cell's attachment to the force sensor using the same surface chemistry techniques.

Two types of surface chemistry may be provided in accordance with embodiments of the invention: The first type utilizes the hydrophobic nature of the polymer and the hydrophilic nature of the metal pads. Such techniques may be set forth in further detail in Tan [P5]. The second type utilizes thiol-gold chemistry to form Self-Assembled Monolayers (SAMs) on the metal pads. Such a type is described in Mrksich [P6].

The gold squares that make up the cell contact area on the relatively rigid area and on the force sensors are initially deposited on silicon-nitride and the polymer layers that make up the force sensor are deposited on top of the gold squares. When the force sensors are suspended using the hot, dilute hydrofluoric acid etch described above, the surface of the gold squares to be used for the surface chemistry described above is exposed. The cleanliness and hydrophilic nature of the gold surface is critical for the surface chemistry. There are a couple of techniques that are critical for ensuring the cleanliness and hydrophilic nature of the gold surface.

An adhesion layer must be used to ensure the gold adheres to the silicon-nitride during fabrication. Titanium is a commonly used adhesion promoter for gold on silicon-nitride. However, after the force sensor is suspended the titanium adhesion layer must be removed in order to expose the gold pad. The hot, dilute hydrofluoric acid etch selectively removes the titanium without removing or damaging the gold.

An alternative to the titanium adhesion layer is an organic molecule containing a sulfur atom and a silane group, such as mercapto-tri-methoxy-silane (MPTS). Typically the MPTS is blanket deposited over a silicon or silicon-derivative surface using a solvent solution (such a toluene). The gold layer is then blanket deposited over the surface and patterning of the gold follows using lithography and a gold etch process. These techniques are described in Ling [P7].

The above-described techniques may be insufficient for this process and application for two reasons: first, it may be necessary to pattern sub-micron features in the gold pads which is hard to do using an etch method—liftoff is preferable. Second, there is a layer of gold alignment marks on the wafer that are needed for multiple layer steps, and the etch process would remove those alignment marks as well. To solve these problems, embodiments of the invention utilize a MPTS deposition process that is compatible with metal deposition and patterning by lift-off. The critical step is to deposit the MPTS layer after developing the resist using an aqueous solution with 0.1% acetic acid, which is described in a data sheet available from the Gelest Corporation (also see [P20]-[P22]). The aqueous solution does not damage the resist layer. This process works well with electron beam resists such at PMMA and with i and g line photoresists such at AZ5214e. Accordingly, embodiments of the invention deposit MPTS from an aqueous solution for this purpose.

Microfluidics

Microfluidic valve and pump systems such as those used in embodiments of the invention have been described before and have also been used to implement a cell sorting system [P8]-[P18]. In this regard, references [P8]-[P18] describe a technology used to build multilayer silicone based microfluidics with multiple flow channels, flow modalities and integrated, and computer driven pneumatic controls.

However, none of the prior art systems have encapsulated a polymer NEMS force sensor in microfluidics. In this regard, embodiments of the invention provide for integrating microfluidics with NEMS force sensors.

The microfluidics serve a number of critical functions. Firstly, microfluidics enable delivery of individual cells to specific force sensors. Secondly, microfluidics provide/enable precise control of the chemical environment around the cell/s under study. Precise control is necessary for cell culture (keeping the cells alive). Additionally, precise control adds precision and control when perturbing the cells with pharmacological agents. Third, significant "fan-out" wiring and electronics are needed to extract signals from the force sensors out to a computer for readout and analysis. The microfluidics decouple the "fan-out" wiring from the fluid necessary for cells and biological studies in general.

A minimal microfluidics system can be very simple, consisting of just a few parts and very basic function: In this regard, embodiments of the invention provide for encapsulation of the force sensor to enclose, minimize and control the volume around the force sensor. Further, embodiments may merely comprise a single inlet and a single outlet.

Particular fabrication methods may include partial flow channels that pass completely through the NEMS chip. For this reason, these NEMS devices require encapsulation from two sides. One side of the NEMS device is encapsulated by a glass cover slip with a thin layer of silicone that acts as a glue and seal. The glass cover slip serves a dual purpose: it encapsulates the device and enables high resolution optical microscopy that is compatible with use of the NEMS devices. The other side of the NEMS device, which has the "fan-out" wiring and NEMS devices is encapsulated with multilayer silicone based microfluidics with multiple flow channels, flow modalities and integrated, computer driven pneumatic controls.

Figure 13:
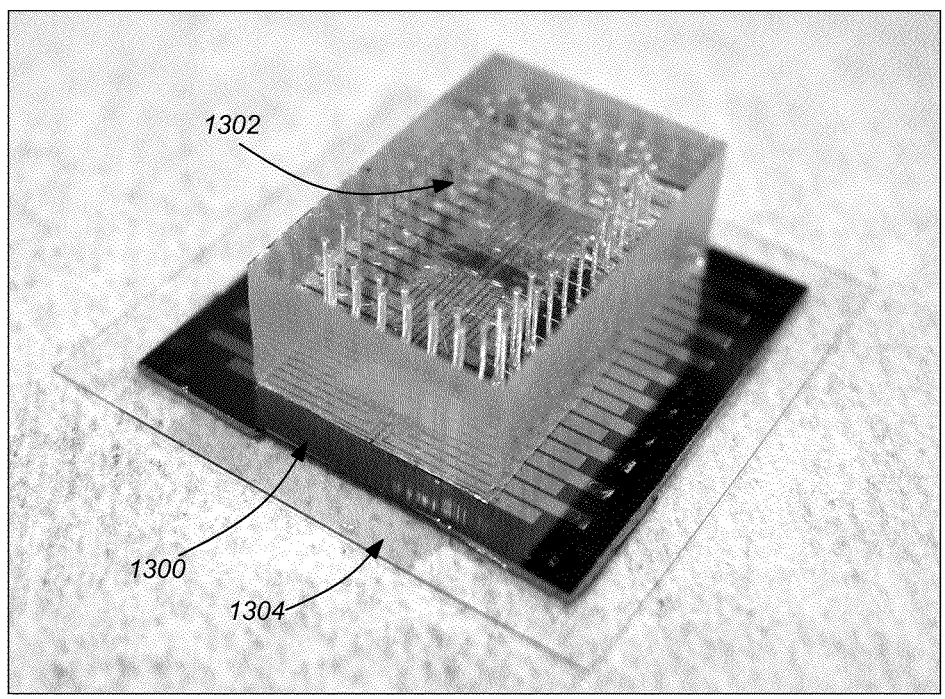
FIG. 13 illustrates a polymer NEMs force sensor embedded in microfluidics in accordance with one or more embodiments of the invention.

FIG. 13 illustrates a polymer NEMs force sensor embedded in microfluidics in accordance with one or more embodiments of the invention. As illustrated, the NEMS chip 1300 is encapsulated. The topside encapsulation 1302 includes multilayer silicone microfluidics with multiple flow channels, flow modalities and integrated computer driven pneumatics. The backside encapsulation 1304 includes a glass cover slip with a thin silicone layer for adhesion and sealing.

Figure 14:
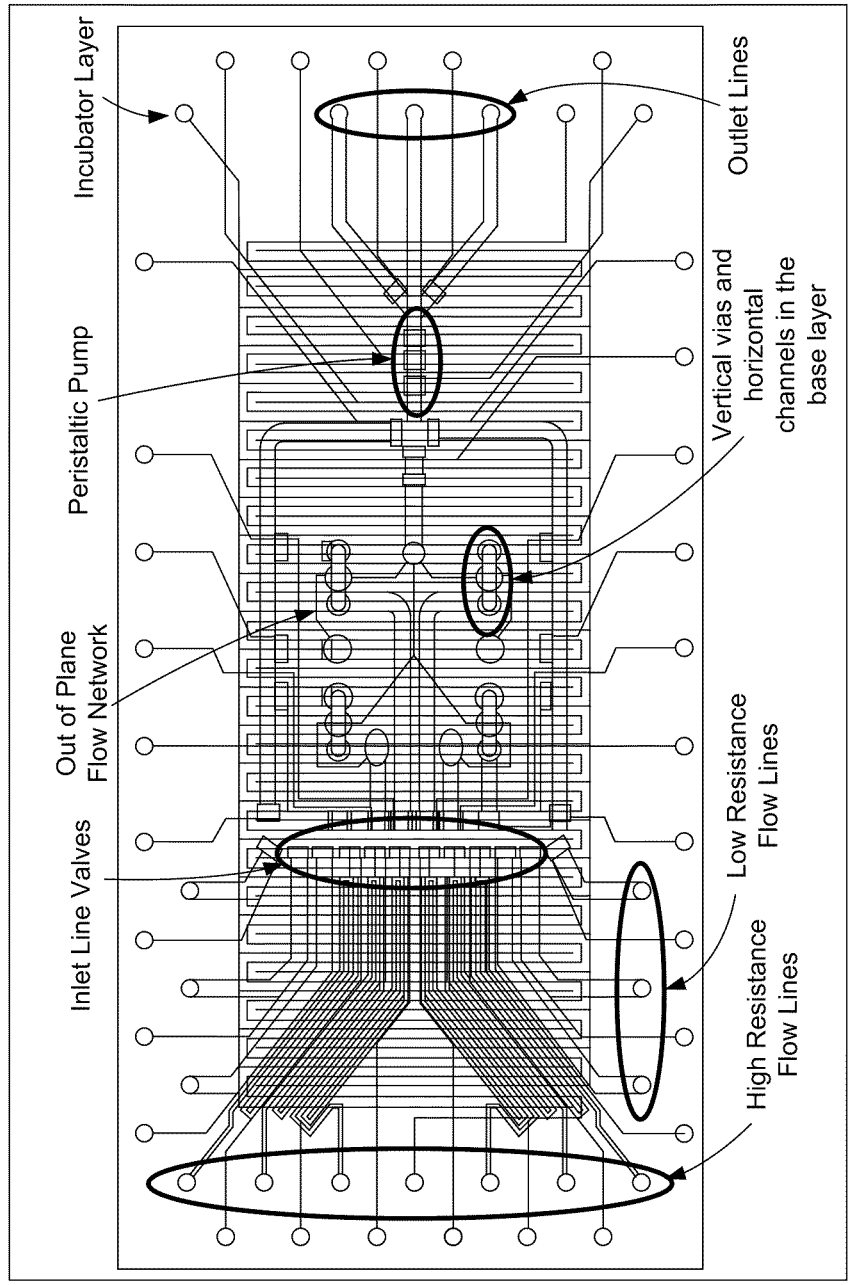
FIG. 14 illustrates a 2D diagram of the four layers that make up the microfluidics in accordance with one or more embodiments of the invention.

A list of the features of the multilayer silicone based microfluidics used on the NEMS force sensor follows. The parts are labeled in FIG. 14, which illustrates a 2D diagram of the four layers that make up the microfluidics in accordance with one or more embodiments of the invention. Four layers of silicone are used to make the microfluidics. The uppermost layer, referred to as the "Incubator Layer" contains interdigitated terminal lines which are filled with water and maintained under pressure in order to saturate the silicone, which is gas permeable, with water vapor and thus prevent evaporation.

The Incubator Layer also contains a zig-zaging through line which can be used to flow gases through the silicone. Flowing mixtures of air and carbon dioxide through the silicone is sometimes necessary for culturing cells within the microfluidics.

The second layer, referred to as the "Flow Layer" and referred to in the drawings as flow lines and outlet lines, contains 12 inlets lines and 3 outlet lines. There are two classes of inlet lines: low fluidic resistance lines with large diameter for flowing cells and the fast flowing of liquids and high fluidic resistance lines with small diameter for slowly flowing liquids. Cells are very sensitive to fluidic shear forces so it is necessary to feed and perturb cells by slowly flowing liquids.

The flow lines are connected to the devices on the NEMS chip by way of "vias" that travel vertically through the third and fourth layers of the chip.

The third layer on the chip, the "Control Layer," contains 34 pneumatic valves which are used to control the flow in the flow layer. The valves are used at flow inlets, outlets, to isolate lines that connect to the individual force sensors, and in combinations to make a peristaltic pump which can be used to precisely meter flow through the flow lines both forward and backward.

There are also "vias" through the control layer that are vertical flow channels that connect the flow layer to the fourth layer and the NEMS chip.

The fourth layer, the "base layer," is in contact with the NEMS chip and contains flow channels which run parallel to the channels in the NEMS chip and encapsulate the NEMS device while leaving it suspended.

The channels in the base layer contain vertical portions that connect to the "vias" through the control layer and horizontal portions, which run along the NEMS chip.

The base layer also includes a set of high resistance flow channels that allow slow liquid flow to pass by the NEMS force sensor perpendicular to the plane in which the sensor senses forces and out of the plane of the sensor. The purpose of this "out of plane" flow network is to enable fluid flow and reagent exchange for cells on the force sensor that does not mechanically perturb the NEMS force sensor.

Thus, as described above, a microfluidic system is used for various purposes. In addition to that stated above, the microfluidic system may be used to position a cell where desired.

The target location for positioning can be any small object or surface upon which it is desirable to place a single cell. It can range in size from as small as ~100 square microns up to 10,000 square microns or larger.

A microfluidic channel must pass over the target area. The microfluidic channel confines the fluid flow, and thus cell location, in two directions. The confined geometry of the microfluidic channel reduces the Reynolds number for flow through the channel below 1. Thus the flow through the channel is laminar and the cell can be moved back and forth—reversibly—along a flow line without convective flow moving the cell in an uncontrolled manner.

In one or more embodiments, the valves may be positioned along the flow channel so that the region around the target location can be sealed off from the rest of the microfluidic system once the cell has been positioned over the target area. Sealing a small region around the target area ensures that unintended flow with not move the cell away from the target area while it is settling.

Further, as described above, a peristaltic pump, integrated into the microfluidic channel, may be used to control the fluid flow and thus the cell's location. The pump can be operated forward or reverse to move the cell forwards and backwards along a flow line until it is located over the target area. Clearly the cell must be on a flow line which passes over the target area, if the target area is centered in the microfluidic channel this is not a difficult condition to meet. The minimum resolution of the cell positioning system is determined by the displacement volume of one of the valves in the peristaltic pump and the channel cross section over the target area.

Once the cell has been positioned over the target location, valves are used to seal off the flow channel around the target area. Gravity will gently lower the cell onto the target location.

Figure 15:
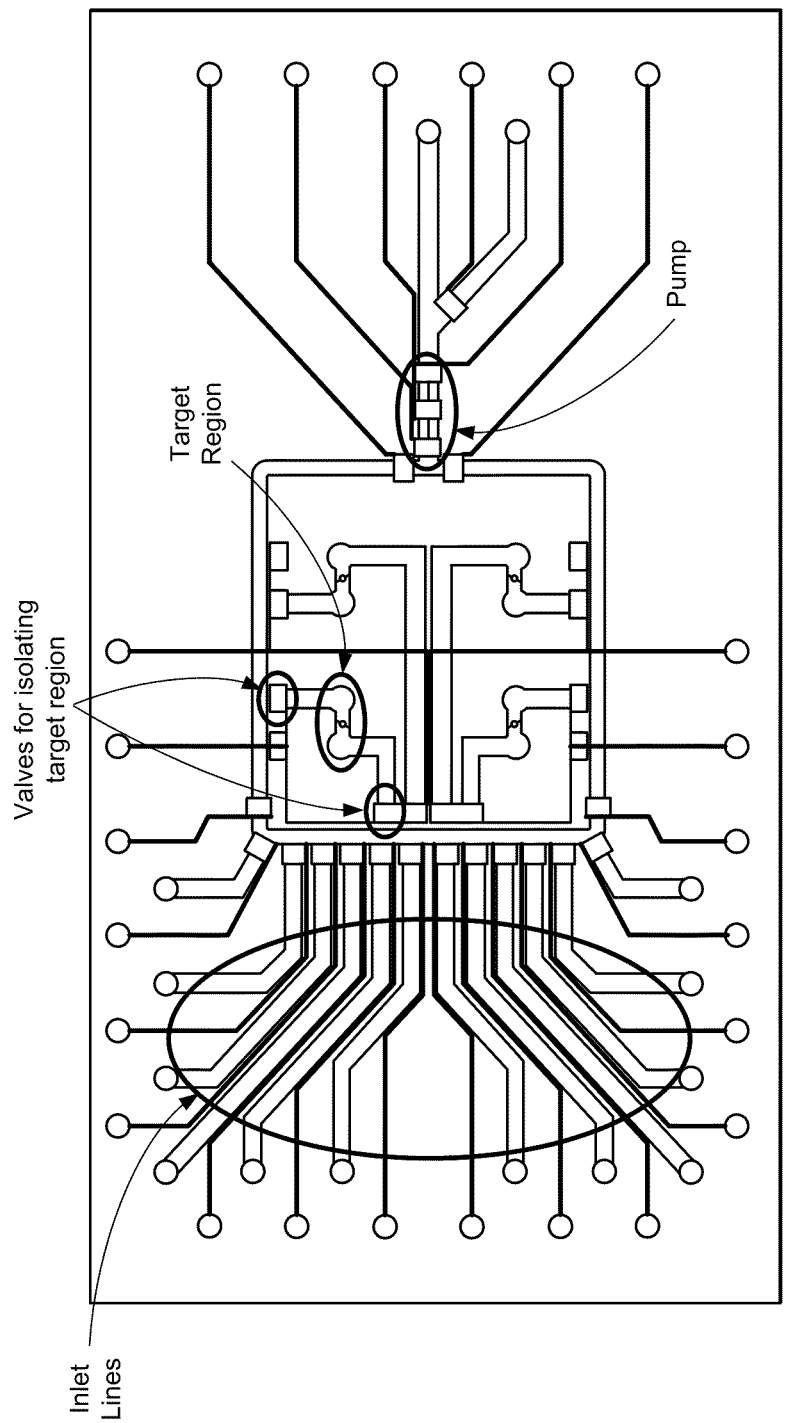
FIG. 15 illustrates a system used to position NIH 3T3 fibroblast cells on plastic NEMs devices in accordance with one or more embodiments of the invention.

FIG. 15 is a schematic of a system utilized to position a cell in accordance with one or more embodiments of the invention. In FIG. 15, the system is used to position NIH 3T3 fibroblast cells on plastic NEMs devices with a target area of 1200 square microns. Similar to FIG. 14, there are 12 inlet lines on this system, four individually addressable target areas, one peristaltic pump and two outlet lines. One of the inlet lines is used to position a cell in the channel with the target area and the peristaltic pump is used to finely position the cell over the device.

Force Measurement Results

As described above, one or more embodiments of the invention may provide for fabricating a device and high yields have been demonstrated (>60%). Successful micro-fluidic encapsulation is routine and consistently performed at very high yields, (>90%). The force sensing capabilities of the devices have been tested and calibrated by perturbing the force sensors with glass micro-needles mounted on piezo-electric actuators, data shown in FIG. 6A. The force sensors have been tested in micro-fluidics be measuring their response to shear forces generated by fluid flow. The force sensors have been successfully used to measure forces exerted by individual adherent cells and to study the mechanical response of those cells to cytoskeleton perturbing reagents such as Cytochalasin D.

Data of force measurement from a single cell have shown a stable force in growth media, collapse of that force when the cytoskeleton disrupting agent Cytochalasin D is introduced, and the recovery of the force when the Cytochalasin D is removed. Such measurements were performed with 200 pN force resolution—an improvement of 25 fold over prior art—and 10 ms time resolution—and improvement of 300 fold over prior art.

Figure 16:
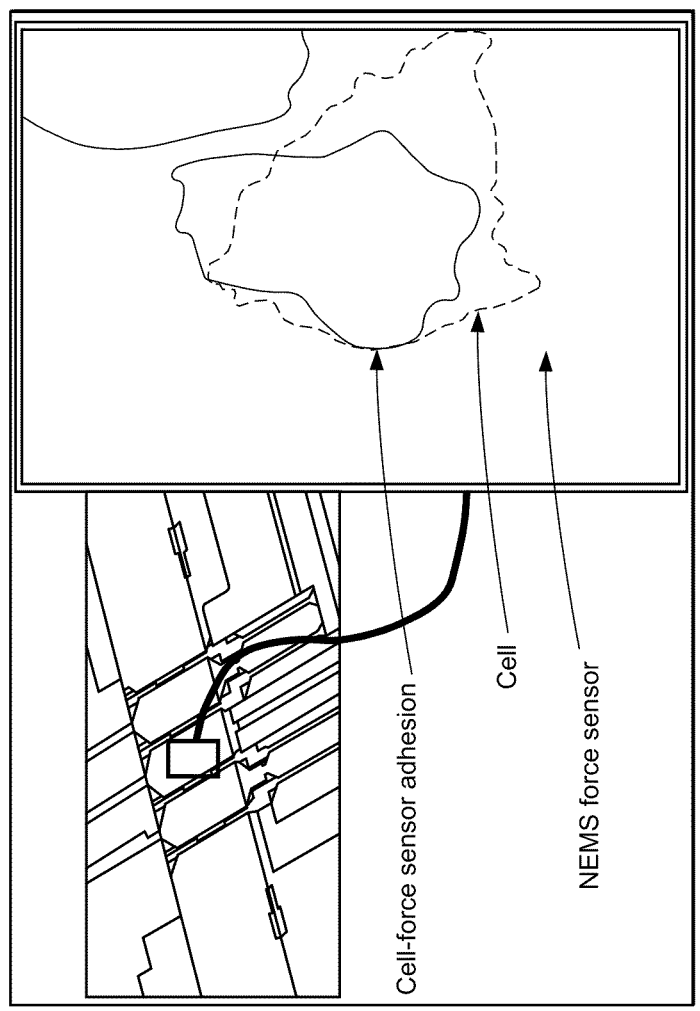
FIG. 16 shows a SEM image of a dry force sensor prior to micro-fluidic encapsulation and a fluorescent image of a cell attached to the force sensor on a micro-fluidics encapsulated device in accordance with one or more embodiments of the invention.

FIG. 16 shows a SEM image of a dry force sensor prior to micro-fluidic encapsulation and a fluorescent image of a cell attached to the force sensor on a micro-fluidics encapsulated device.

Figure 17:
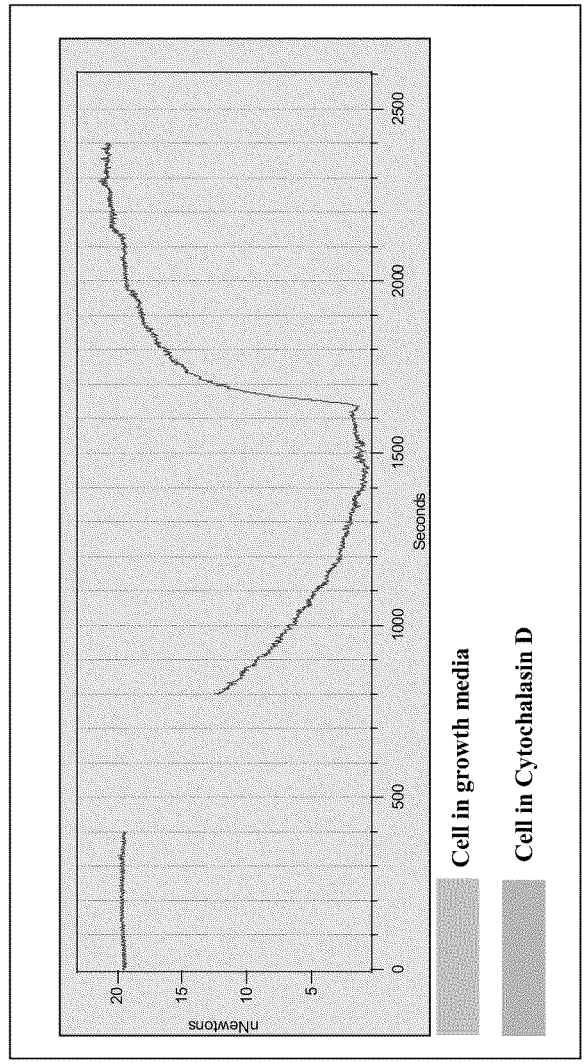
FIG. 17 shows force vs. time data from a single cell showing a stable force in growth media, collapse of that force when the cytoskeleton disrupting agent Cytochalasin D is introduced, and the recovery of the force when the Cytochalasin D is removed in accordance with one or more embodiments of the invention.

FIG. 17 shows force vs. time data from a single cell showing a stable force in growth media, collapse of that force when the cytoskeleton disrupting agent Cytochalasin D is introduced, and the recovery of the force when the Cytochalasin D is removed. These measurements were performed with 200 pN force resolution—an improvement of 25 fold over prior art—and 10 ms time resolution—and improvement of 300 fold over prior art.

Vacuum Insulating Polymer-Based Micro-Biocalorimeter Integrated with Microfluidics In addition to the above described force sensors, one or more embodiments of the invention further provide for the use of a micro-biocalorimeter that is vacuum insulated, polymer based, and integrated within microfluidics.

As described above, a calorimeter is a device for the measurement of the heat capacity of materials and the enthalpy change in chemical reactions. Calorimetry is a technique widely used by the pharmaceutical industry, biologists and chemists to study the kinetics of biochemical reactions and the reaction of living organisms and tissues to chemicals (e.g., drugs). In this regard, calorimeters have been used in diverse research areas in biology, such as studies of thermodynamic properties, structure and interactions of proteins because of universal nature of heat generation in biochemical reaction and simple preparation of samples.

However, the use of calorimeters has been limited due to its large consumption of sample and long measurement time, typically >1 mL and 1 hour. Microfabrication techniques have made it possible to build small scale calorimeters to overcome these disadvantages. In these calorimeters, samples are prepared as either droplets on micro-size sensing regions or flow through microfluidic channels. Microfabricated thermometers are used to achieve very good temperature sensitivity. Measurement sensitivity of these calorimeters, however, are not as good as large scale calorimeters, due to large device heat capacity and thermal conductance. There has been no serious attempt to increase sensitivity by minimizing the heat loss of the sample.

One or more embodiments of the invention provide a fabrication and operation of a highly sensitive heat conduction calorimeter with vacuum insulation, which can detect enthalpy change of reactions from ~3.5 nanoliter (nL) liquid sample. In this regard, a parylene polymer-based micro-biocalorimeter is integrated with microfluidics (also referred to as a "CIT calorimeter") that is capable of performing batch, isothermal titration and differential scanning calorimetric measurements on 50 picoliter (pL) to 100 nanoliter (nL) volumes of chemical reagents and living tissues. The calorimeter could also be configured as a detector of chemicals and hazardous reagents. The major advantages of the CIT calorimeter over existing biocalorimeters are the following:

1. Small reagents volume: The volume of reagents used in the CIT biocalorimeter is significantly lower than that in conventional commercial biocalorimeters such as a MicroCal VP-ITC [CIT 1] which uses ~1 microliter (µL) of reagents. For many applications, this is very useful because reagents (such as a newly synthesized protein) could be very expensive and scarce.

2. Liquid delivery by microfluidics: The use of a microfluidics system with on-chip pumping and valves enables automated delivery of liquid over other biocalorimeters that require manual injection. [CIT 1] [CIT 2]. It also provides efficient delivery of small amounts of liquid at relatively low cost compared to the traditional, "robotic-pipette" systems such as that used by the MiDiCal microplate system developed by Vivactis. It furthermore allows easy interfacing with existing pipelines (e.g., a water distribution system) from which it could draw samples for analysis. Devices including sensor and microfluidic controls can be packed in very small volume and be easily developed as a hand-held detector.

3. Simultaneous operation of multiple calorimeters: Because the calorimeters are produced on inexpensive glass substrates by standard semiconductor processing technologies, the user could obtain and operate multiple (e.g., 100 to 1000) calorimeters simultaneously. This greatly improves the efficiency of calorimetric measurement. Moreover, this low cost calorimeter is disposable, easy to use and saves cost on cleaning 4. Large bandwidth: The microcalorimeter promises a fast response at ~1 kHz. It could be used to trace the reaction of a cell to its surroundings.

Overview—Design of the CIT calorimeter

The three major building blocks of the calorimeter are the thermometry, the microfluidics and the thermal isolated reagents compartment.

Microfluidics

The main microfluidic body is built with parylene. Microfluidic control, such as on chip pumps and valves, can be made in different ways. One way is to build a PDMS microfluidic control and combine the control with a parylene channel. Another way is making on-chip electrostatic-actuated pumps and valves on silicon or glass substrates by optical lithography and parylene and metal deposition.

Thermometry

The thermometry is used to determine the temperature change due to the reactions of biochemical reagents. Thermopile thermometry of two thermoelectric components, such as gold and nickel, can be used which is easy to fabricate and reliable. The thermopile thermometry with metallic thermoelements generally provides a responsivity of 200 to 500 µV/K. This is corresponded to a temperature sensitivity of ~0.1 mK.

Thermal Isolated Reagents Compartment by Vacuum and Air Gap

The most critical part of a calorimeter to achieve pL-scale reagent volumes is the design of the compartment for reagents. Because of the small volume of reagents and/or living tissues involved, the enthalpy change due to the biochemical reactions is very low. The typical power of a biochemical reaction is 1 to 10 nW for 100 pL of reagents. To generate a resolvable temperature gradient from the power, the total thermal conductance of the compartment to the environment must be very low at ~1 µW/K. Thus, the average conductivity of the constructing material is 0.03 W/m K.

The most common forms of thermal isolation used for calorimeters are thermally resistive enclosures, [CIT 1] air cushions (generated by membranes)[CIT 2][CIT 3] and insulating substrates. Such techniques are not readily applicable to a 100 pL calorimeter. A resistive enclosure for a 100 pL volume has to be made as small as the volume itself. The silicon nitride membranes used by the existing calorimeter are themselves too conductive (thermal conductivity of silicon nitride is 30 W/m K). Finally, everyday insulating materials such as foam are composed of air sacs that are as big as the calorimeter itself and could not be used as the substrate.

Figure 18:
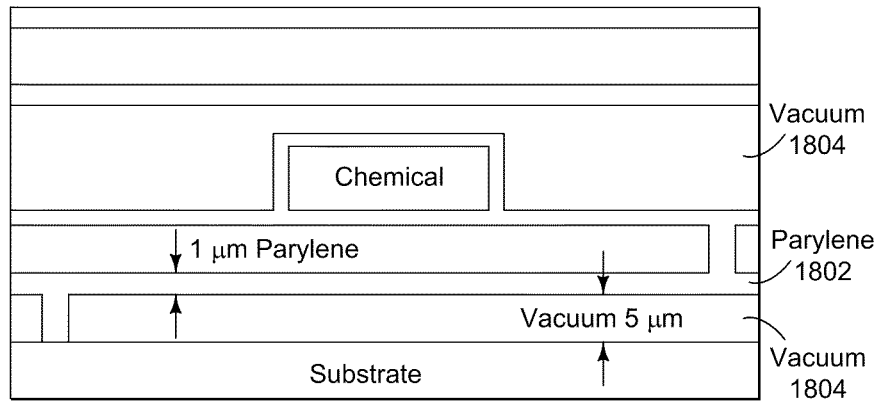
FIG. 18 illustrates a cross section of such a multilayer parylene calorimeter compartment in accordance with one or more embodiments of the invention.

In one or more embodiments of the invention, a multi-layered parylene structure is used for vacuum isolation, the suspended parylene structure is fabricated by standard semiconductor processing techniques and extends outward for ~500 µm. FIG. 18 illustrates a cross section of such a multi-layer parylene calorimeter compartment in accordance with one or more embodiments of the invention. As illustrated, the parylene 1802 poles connect separate layers for mechanical support. The thermometer (not shown) is on the parylene membrane 1802 directly under the chemicals. The chemicals are brought into the chamber through a microfluidics channel (not shown) and isolated from the channels by valves (not shown).

An inexpensive mechanical pump is applied to create a vacuum 1804 of 1 mbar. This is possible because of the low gas permeability of parylene 1802. The 1 mbar vacuum, coupled with the small dimensions of the layer, has a thermal conductivity of 0.0005 W/m K. The resultant compartment has a thermal conductance of 0.1 µW/K from the vacuum 1804 (residual air) and 0.4 µW/K from the parylene membrane 1802. Thus, the total thermal conductance of the compartment is 0.5 µW/K.

One can emphasize the unique nature of parylene for construction of the compartment because of its low thermal conductivity, gas permeability and available valve structures. Many polymers, such as SU-8, could form similar structures. However, since they could not form valves, the reagent compartment is not cut off from the fluidic channels, which results in large thermal leaks. On the other hand, common microfluidics materials, such as PDMS, are highly permeable to gas and very soft, and so could not support a vacuum.

Figure 19:
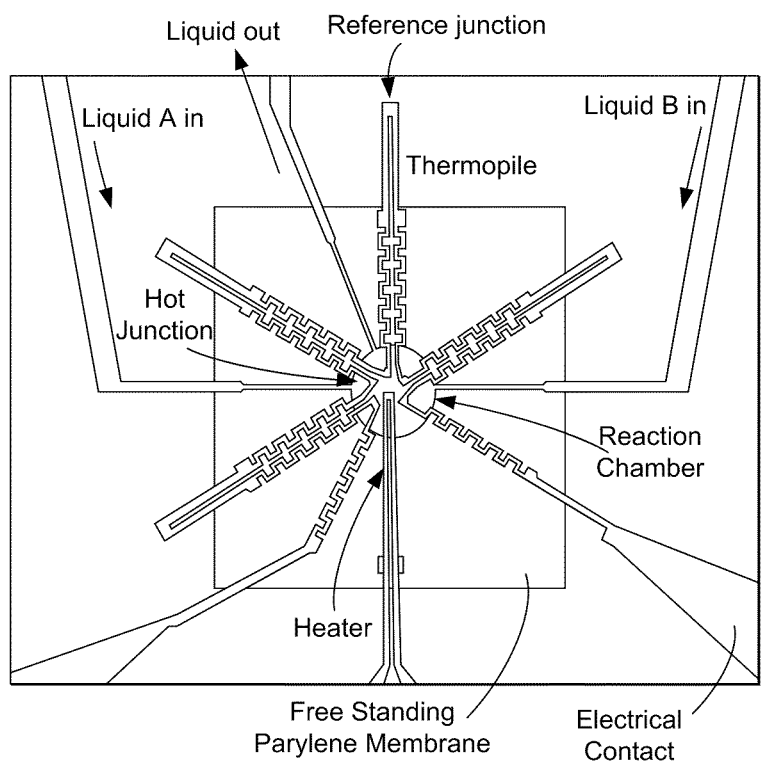
FIG. 19 shows the reaction chamber on a suspended parylene membrane, the microfluidics channels for fluid delivery, and the thermopile for sensing heat release in accordance with one or more embodiments of the invention.

In addition, a prototype of a parylene microcalorimeter is illustrated in FIG. 19. FIG. 19 shows the reaction chamber on a suspended parylene membrane, the microfluidics channels for fluid delivery, and the thermopile for sensing heat release. The additional layers for building the vacuum pocket are not shown. As illustrated, a simple structure having two input channels and a single output channel is illustrated. The two inputs are combined in the reaction chamber and heated. The electrical contact is used to measure and output the enthalpy change.

Detailed Description—CIT Calorimeter

The above description provides an overview of a parylene microcalorimeter in accordance with embodiments of the invention. A detailed description of such a calorimeter follows.

Figure 20:
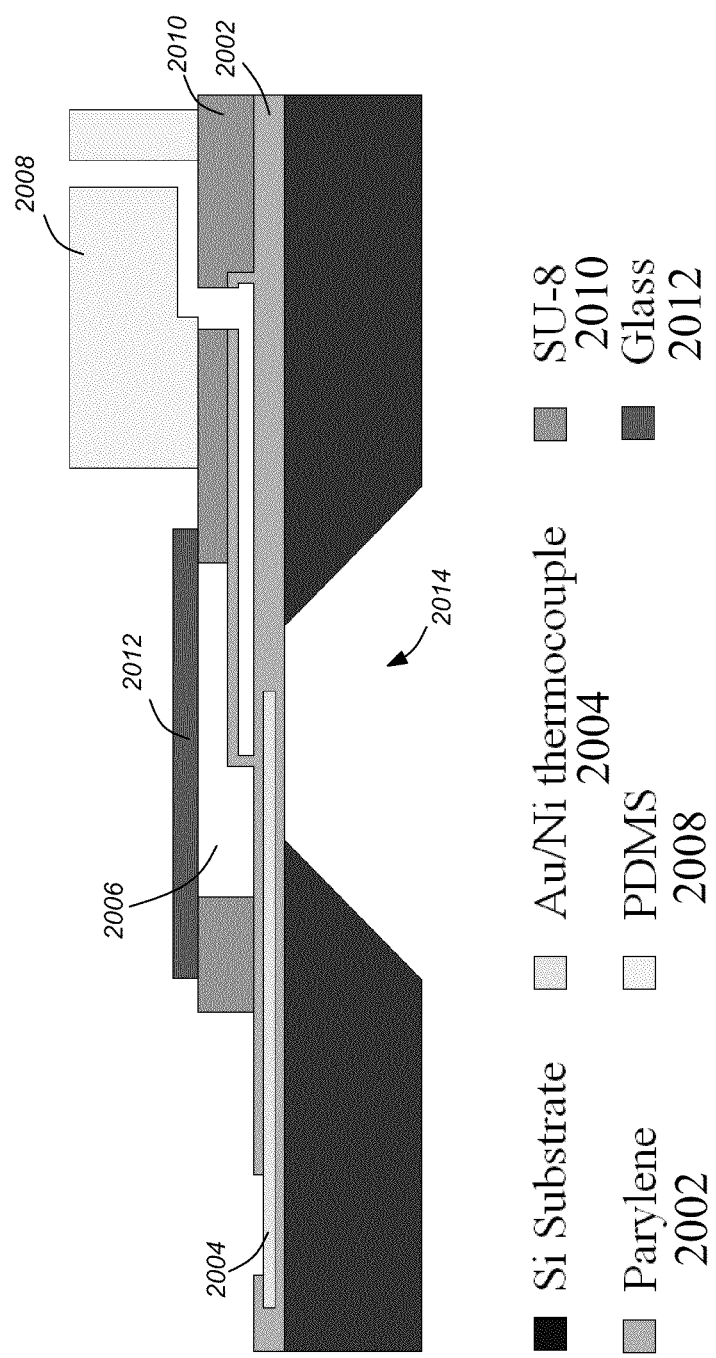
FIG. 20 illustrates a schematic of a calorimeter in accordance with one or more embodiments of the invention.
Figure 21:
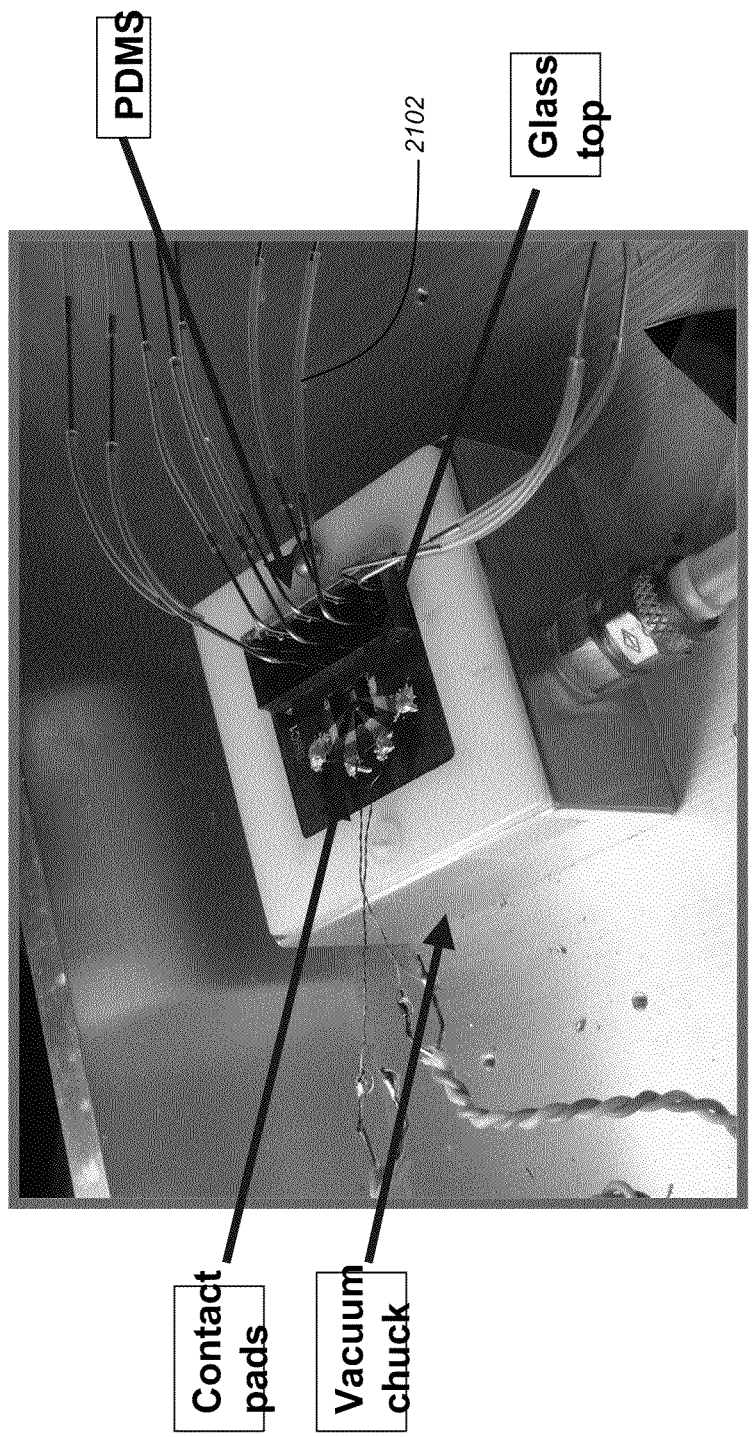
FIG. 21 illustrates a whole chip embodying the calorimeter in accordance with one or more embodiments of the invention.
Figure 22:
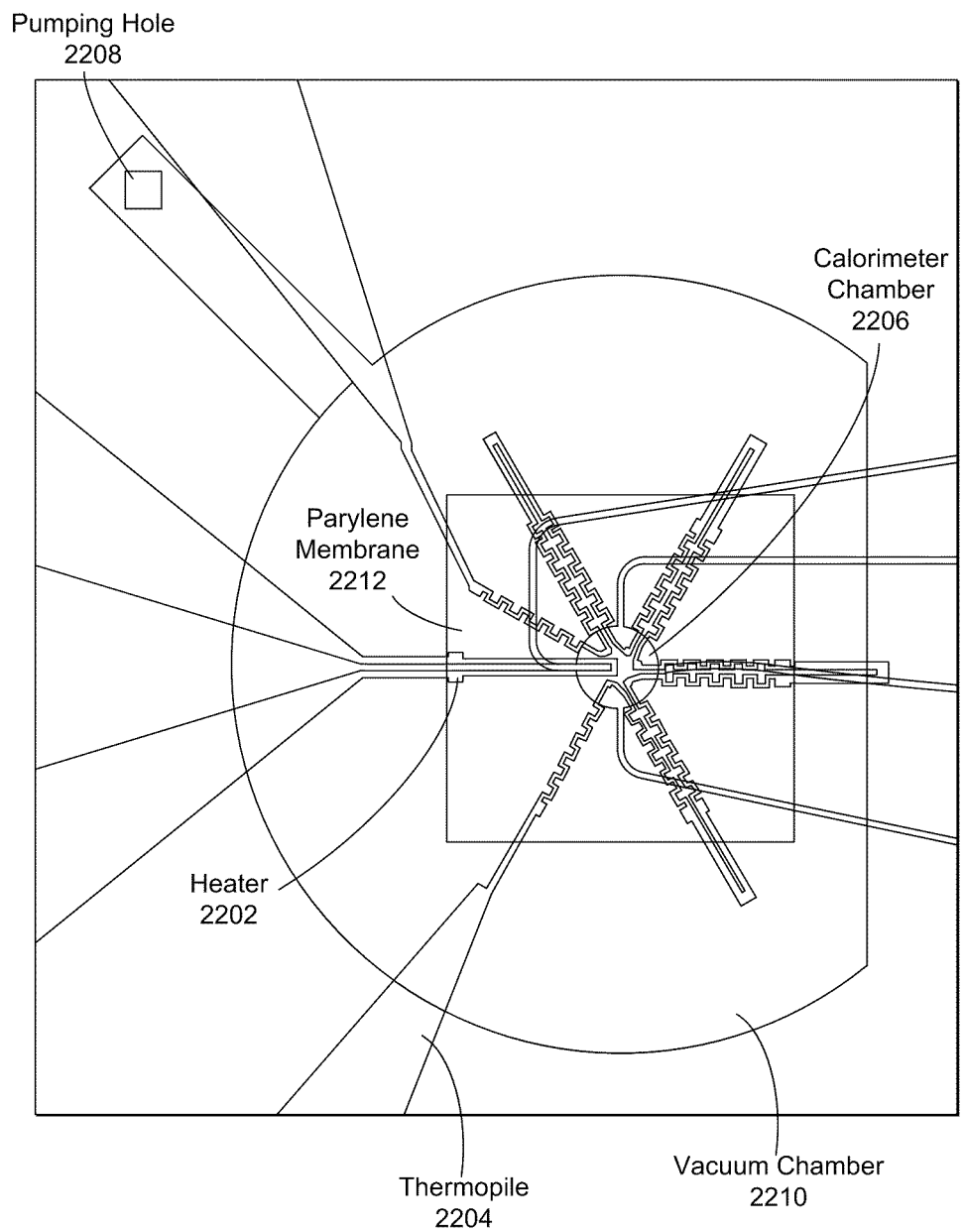
FIG. 22 illustrates a detailed view of a calorimeter chamber and electric sensor built on a parylene membrane in accordance with one or more embodiments of the invention.

The calorimeter consists of thin film thermopile, parylene-polydimethylsiloxane (PDMS) hybrid microfluidic system and vacuum insulation structure. FIG. 20 illustrates a schematics of a calorimeter in accordance with one or more embodiments of the invention. FIG. 21 illustrates a whole chip embodying the calorimeter in accordance with one or more embodiments of the invention. FIG. 22 illustrates a detailed view of a calorimeter chamber and electric sensor built on a parylene membrane in accordance with one or more embodiments of the invention. The following description refers to aspects of FIGS. 20-22.

Both sides of the parylene membrane 2002 are under vacuum during measurement. Thermopile 2004 is buried between two parylene layers 2002 and protected from the sample, which is placed into the chamber 2006. Au/Ni metallic thermopile 2004 is chosen as a thermometer because of fabrication convenience and low electric noise. 5 thermocouple junctions are connected in parallel to give ~110 µV/K temperature coefficient ($\epsilon$).

FIG. 21 illustrates an image of a calorimeter implementation in accordance with one or more embodiments of the invention. As illustrated, the fluid is placed into the channels via various fluidic distribution members 2102. After sensing the enthalpy change, the calorimeter is used to produce an electrical output on contact pads 2104. The glass top and vacuum chuck serves to seal the chip and create a vacuum chamber as described herein. Similarly, FIG. 22 illustrates the heater 2202, electrical contacts/thermopile 2204, reaction/calorimeter chamber 2206, pumping hole 2208, vacuum chamber 2210, and parylene membrane 2212 used to measure the enthalpy change.

Figure 23:
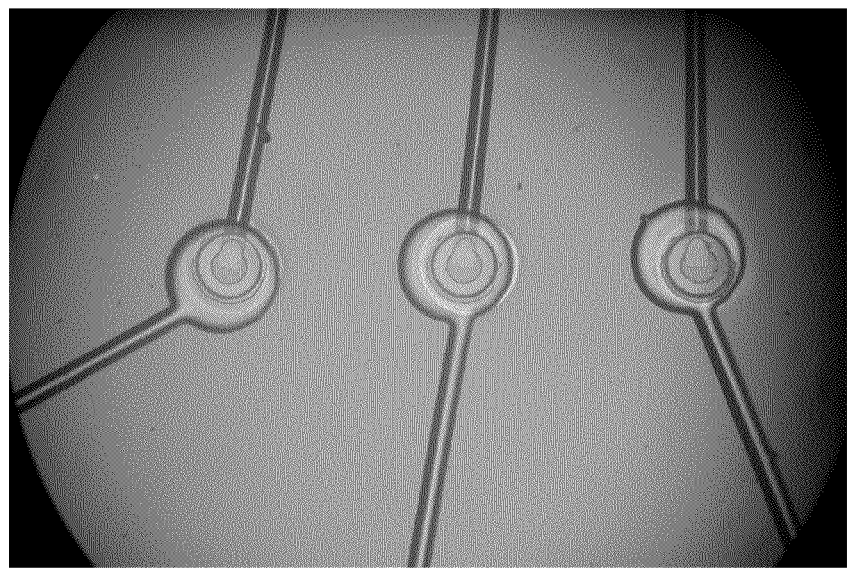
FIG. 23 is an image illustrating an alignment of the fluidic channels on parylene channels in accordance with one or more embodiments of the invention.

Referring again to FIG. 20, parylene 2002 is used to build the microfluidic channel and calorimeter chamber 2006, because parylene 2002 has many advantages in property such as chemical inertness, biocompatibility. However, parylene is not compliant as PDMS and there may not be an easy mechanism to incorporate valves or pump. Thus, PDMS microfluidic valves and pumps may be combined with parylene microfluidic channels for better manipulation of samples. To secure the PDMS microfluidic structure 2008, the parylene channel 2002 is planarized with thick SU-8 2010. PDMS fluidic channels 2008 are aligned on parylene channels 2010 opening and further cured to be bonded on SU-8. FIG. 23 is an image illustrating an alignment of the fluidic channels on parylene channels (i.e., a parylene-su8-pdms junction) in accordance with one or more embodiments of the invention.

Figure 24:
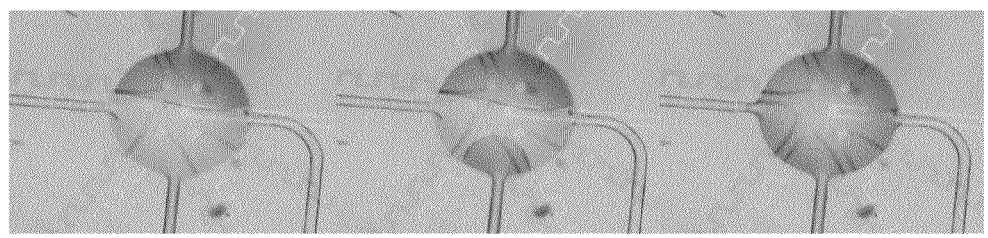
FIG. 24 illustrates three images of merging two reactants in accordance with one or more embodiments of the invention.

PDMS peristaltic pumps are used to move liquid through the channel. For a batch mode measurement, a reactant is used to fill up to half of the reaction chamber 2006, and then second reactant is delivered to the reaction chamber 2006 (e.g., via the microfluidic channel created via PDMS 2008, SU-8 2010 and parylene 2002. The second reactant is merged with the first reactant. FIG. 24 illustrates three images of merging two reactants in accordance with one or more embodiments of the invention.

Reaction from reactants in the channel may be ignored because its volume is very small compared to total chamber volume. Reactants far from chambers are considered as not participating in reaction due to long diffusion time.

For a microscale calorimeter, it's very challenging to keep the heat capacity of addenda small while reducing the sample volume. For instance, when the sample is surrounded by bulky microfluidic material, much of sensitivity is lost due to huge heat loss to chamber wall. Parylene microfluidic channels can have only ~1 μm thick wall, so it can reduce heat loss significantly and even replace SiN membrane, which is used for the most of microscale calorimeter even though it is quite conductive. Even more reduction of the heat loss can be accomplished by accommodating on-chip vacuum capability. Parylene thin film 2002 can give very low gas permeability and mechanical strength, which enables the application of vacuum insulation on the device. With nanoliter scale sample volume, the surface to volume ratio of the sample becomes significantly large, resulting in significant heat loss from the surface. This implies that even heat loss through air to the environment can significantly affect the sensitivity.

Figure 25:
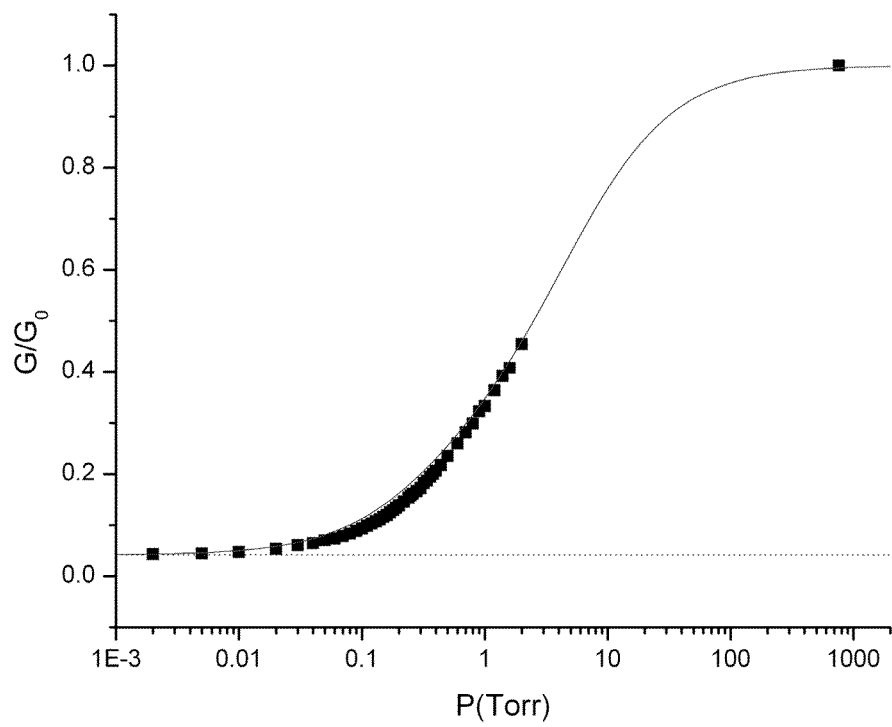
FIG. 25 shows the effect of a vacuum on device thermal conductance in accordance with one or more embodiments of the invention.

FIG. 25 shows the effect of a vacuum on device thermal conductance (G). As illustrated, the amount of conductance improves significantly as the pressure P vacuum is applied. The on-chip vacuum chamber has two regions. The region above the parylene membrane 2002 is defined by the SU-8 2010 on the side and the glass ceiling 2012. The region 2014 below the membrane 2002, formed by KOH etching for a SiN membrane, is sealed by an o-ring and a vacuum chuck. A 2 μm thick parylene channel provides enough mechanical strength and isolation of gas or liquid inside the chamber 2006 from the vacuum. One can observe chamber volume change due to parylene stretching under pressure difference between the inside and the outside of the chamber 2006. The volume after applying a vacuum was measured to be ~3.5 nl. The small membrane left upper corner was built, and removed later, to pump the upper region.

To calibrate the thermometer signal, thermoelectric voltage response was measured over electric power applied on the gold heater. The heat power sensitivity (Sp), which is defined as voltage output over applied power, was 5V/W. Since $S_p = \epsilon/G$, both increase in &, for example use high Seebeck coefficient material and decrease in G can give better sensitivity. However, materials with a high Seebeck coefficient, such as doped Si, usually has high electric resistivity and give large electric noise on thermoelectric voltage measurement. The resistance of Ni/Au thermopile was ~1.1 kΩ and the noise at 1 Hz was ~10 nVrms/√Hz, which corresponds to equivalent power noise of ~2 nW/√Hz.

Thermal conductance was 22 μW/K. According to the finite element simulation, it can be as small as 5 μW/K if the air conductance was minimized. This result implies the vacuum insulation did not reach its best with only one layer of vacuum sac. Multiple layers of vacuum sac or higher vacuum is expected to improve the overall sensitivity by lowering the thermal conductance.

In view of the above, embodiments of the invention provide a highly sensitive microfluidic embedded calorimeter. Integration of a microfabricated thermal sensing element, microfluidic system and on-chip vacuum structure enable the ability to measure the nanocalorie scale heat of reactions from 3.5 nl samples.

Device sensitivity on thermometer side has not pushed to its limit. Thermopile material with high Seebeck coefficient and multiplication of signal by increasing number of thermocouple junction may provide increased temperature sensitivity. In addition, careful balancing of thermal conductance of each element may provide a further reduction in thermal conductance.

Although single device operation are described herein, multiple devices may also used to increase throughput or to be deployed as detector array. All of the fabrication steps are compatible with mass production. The device concept can also be applicable to different type of calorimeters such as isothermal titration calorimeter (ITC), differential scanning calorimeter (DSC) and flow calorimeter, with simple geometry change.

Fabrication and Use—CIT calorimeter

To make a suspended parylene membrane, one first builds a 1.5 mm square SiN membrane with a double side polished SiN wafer. This SiN membrane is removed by Reactive Ion Etch (RIE) at the end of fabrication steps. 1 μm thick parylene is deposited on the SiN with PDS 2010 LABCOTER® 2, parylene coater. As a thermometer and a resistive heater, 90 nm thick Ni and 80 nm thick Au are e-beam evaporated on parylene. 4 nm thick Ti is evaporated as adhesion layer for both Ni and Au. They are patterned by photolithography and chemical wet etch. A 1 μm thick $2^{nd}$ parylene layer is coated as a protective layer. The parylene microfluidic channel can be built in conventional method. A 15 μm thick photoresist is spun and patterned into the microfluidic chamber and the channel structure. A $3^{rd}$ parylene layer, 2 μm thick, is deposited on the photoresist to build the parylene microfluidic channel. A ~80 μm thick SU-8 structure is built on top of the parylene microfluidic structure to planarize the surface and to construct the vacuum chamber.

Several etching steps can be conducted by RIE. First, the parylene microfluidic channel opening area was etched (O2 plasma 150 mT, 140 W). The photoresist filling inside the channel is removed using propylene glycol methyl ether acetate (PGMEA). After the microfluidic channel is cleared, parylene covering the electric contact area is etched (O2 plasma 150 mT, 140 W). Finally, the parylene membrane is suspended alone by etching away SiN underneath (CF4 plasma 120 mT, 140 W). The vacuum chamber region is sealed with a glass slide using UV curable glue.

Electrical Measurements may be obtained using the device described herein. Thermal conductance and the device time constant is measured by applying step function heating voltage to the heater. Calorimeter temperature response to applied power can be represented as $$\Delta T = \frac{P}{G}(1 - e^{-\frac{t}{\tau}}).$$

For heat of reaction measurement, thermoelectric voltage can be directly recorded by oscilloscope. FEMTO low noise preamplifier with 2.3 nV/√Hz input noise can be used to amplify the signal.

Logical Flow

Figure 26:
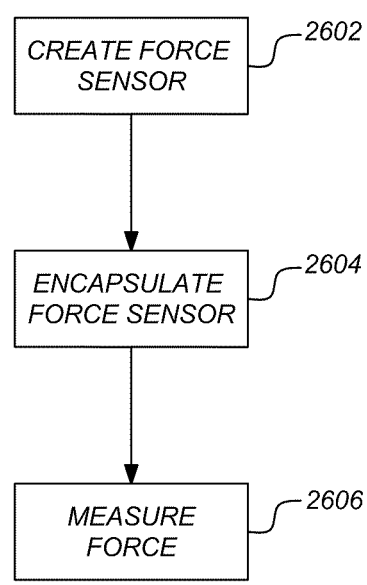
FIG. 26 illustrates the logical flow for creating and utilizing a microfluidic embedded NEMS force sensor in accordance with one or more embodiments of the invention.

FIG. 26 illustrates the logical flow for creating and utilizing a microfluidic embedded NEMS force sensor in accordance with one or more embodiments of the invention. At step 2602 the force sensor is created. Such a force sensor is comprises a deformable member that is integrated with a strain sensor. The strain sensor coverts a deformation of the deformable member into an electrical signal.

The deformable member may be a doubly clamped beam and the strain sensor may be a piezo resistive strain sensor that is patterned asymmetrically through the doubly clamped beam so as to couple to regions of maximum tensile or compressive strain. The piezo resistive strain sensor may be a c-shape that is patterned in the horizontal plane of the doubly clamped beam and is used to measure in-place forces. Alternatively, the strain sensor may be patterned using a straight line pattern to measure out-of-plane forces.

The force sensor may be fabricated from a polymer. In this regard, the strain sensor may be sandwiched between two layers of polymer to electrically isolate the strain sensor from the fluid in the fluidic environment.

In addition to the above, the force sensor may consist of the deformable member and a transducer used for reading out the electrical signal. In such an embodiment, the deformable member may be a doubly-clamped beam made from two polymer layers and the transducer may be a gold wire sandwiched between the two polymer layers. Further, the force sensor may be fabricated on a silicon-nitride coated silicon wafer and suspended over an opening etched in the wafer. Such an opening comprises part of the microfluidic channel that surrounds the force sensor. Also, the force sensor is suspended from the wafer's surface over a hole etched through the wafer's backside. A contact area on the force sensor may also be defined by a metal region or a grid of metal regions that control where a biological sample exerts a force on the force sensor. The metal layer may adhere to the silicon substrate using an organic adhesion promoter and is patterned using metal liftoff.

In terms of fabricating the force sensor, multiple steps may be involved. A first polymer layer may be deposited onto a silicon-nitride layer coating a silicon wafer. A metal wire may then be deposited (on the first polymer layer) that provides a piezo-resistive element of a strain sensor. A second polymer layer is deposited on the metal wire and the first polymer layer. A hole can then be etched through the wafer's backside. The force sensor can then be defined by creating a polymer structure, from the first polymer layer and second polymer layer, that encapsulates the metal wire, and that is suspended over the hole, by removing the silicon-nitride layer from a portion of the wafer, without damaging the first polymer layer and the second polymer layer. The opening may define part of a fluidic channel that surrounds the force sensor. Further, the hole may be etched through the wafer's backside using potassium hydroxide. The silicon-nitride layer can be removed from a portion of the wafer using a combination of a flourine based plasma and a hot dilute hydrofluoric acid.

A further part of the fabrication process may include depositing a metal layer for controlling cell adhesion to the force sensor. Such a metal layer may consist of a grid of metal squares that control where a biological sample exerts a force on the force sensor.

At step 2604, the force sensor is encapsulated in a microfluidic channel. The channel serves to control a fluidic environment around the force sensor and improves an electrical read out (or enables a precise electrical readout) of the electrical signal from the force sensor.

At step 2606, the force sensor is used to measure the force exerted (e.g., by a biological sample/single cell).

Figure 27:
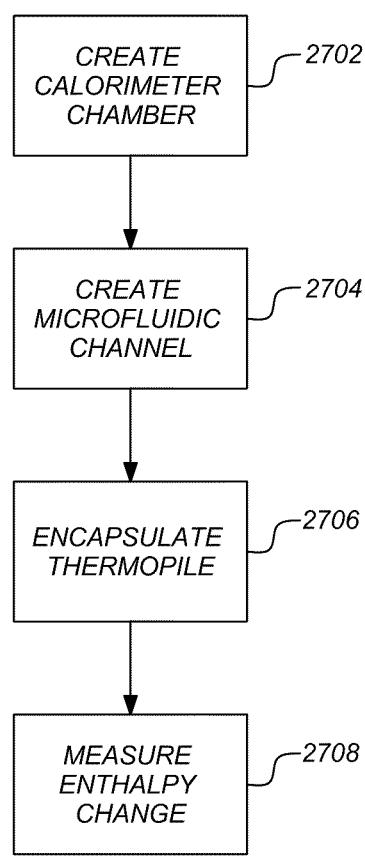
FIG. 27 illustrates a method for utilizing a microfluidic embedded vacuum insulated biocalorimeter in accordance with one or more embodiments of the invention.

FIG. 27 illustrates a method for utilizing a microfluidic embedded vacuum insulated biocalorimeter in accordance with one or more embodiments of the invention.

At step 2702, a calorimeter chamber is created using a parylene membrane. Both sides of the calorimeter chamber are under vacuum during measurement of a sample. Thus, the calorimeter chamber may consist of two regions. A first region adjacent the parylene member can be defined by SU-8 on a first side and glass on a second side. The second region is adjacent the parylene member and can be formed by potassium hydroxide (KOH) etching for a SiN (Silicon nitride) membrane that is sealed.

At step 2704, a microfluidic channel is created. Such a channel is used to deliver a sample to the calorimeter chamber. Further, the channel is built from the parylene membrane.

At step 2704, a thermopile (e.g., a nickel/gold), used as a thermometer, is encapsulated/located between two layers of the parylene membrane and is protected from the sample. Further, multiple layers of vacuum can be utilized to provide further insulation of the sample.

At step 2708, the biocalorimeter is used to measure the enthalpy change of biological samples in the chamber. A PDMS (parylene-polydimethylsiloxane) peristaltic pump can be used to move the sample in liquid along the microfluidic channel to obtain the measurement.

CONCLUSION

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

[1] Roukes, M. Nanoelectromechanical systems face the future. Phys. World 14, 25-31 (February 2001).
[2] Cleland, A. N. & Roukes, M. L. A nanometer-scale mechanical electrometer. Nature 392, 160-162 (1998).
[3] Rugar, D. et al. Single spin detection by magnetic resonance force microscopy. Nature 430, 329-332 (2004).
[4] Yang, Y. T. et al. Zeptogram-scale nanomechanical mass sensing. Nano Lett. 6, 583-586 (2006).
[5] Mamin, H. J. & Rugar, D. Sub-attonewton force detection at millikelvin temperatures. Appl. Phys. Lett. 79, 3358-3360 (2001).
[6] Naik, A. et al. Cooling a nanomechanical resonator with quantum back-action. Nature 443, 193-196 (2006).
[7] Schwab, K. C. & Roukes, M. L. Putting mechanics into quantum mechanics. Phys. Today 58, 36-42 (July 2005).
[8] Tortonese, M., Barrett, R. C. & Quate, C. F. Atomic resolution with an atomic force microscope using piezoresistive detection. Appl. Phys. Lett. 62, 834-836 (1993).
[P1] Landau, L. D. and Lifshitz E. M. *Theory of Elasticity* (1959).
[P2] Thaysen, J. Yalcinkaya, A D, Vettiger, P., and Menon, A. Polymer-based stress sensor with integrated readout. J. Phys. D: Appl. Phys. 35, 2698-2703 (2002).
[P3] Mo Li, H. X. Tang, and M. L. Roukes, Ultra-sensitive NEMS-based cantilevers for sensing, scanned probe and very high-frequency applications, Nature Nanotechnology, vol. 2, February 2007, 114-120 (Jan. 28, 2007).
[P4] D. Martin Knotter and T. J. J. (Dee) Denteneer, Etching Mechanism of Silicon Nitride in HF-Based Solutions, Journal of the Electrochemical Society 148 (3) F43-F46 (2001).
[P5] John L. Tan, Wendy Liu, Celeste M. Nelson, Srivatsan Raghavan, and Christopher S. Chen, Simple Approach to Micropattern Cells on Common Culture Substrates by Tuning Substrate Wettability, Tissue Engineering, Volume 10, Number 5/6, 865-872 (2004).
[P6] Milan Mrksich, Chrisopher S. Chen, Younan Xia, Laura E. Dike, Donald E. Ingber, and George M. Whitesides, Controlling cell attachment on contoured surfaces with self-assembled monolayers of alkanethiolates on gold, Proc. Natl. Acad. Sci. USA Vol. 93, pp 10775-10778 (October 1996).
[P7] T. G. I. Ling, M. Beck, R. Bunk, E. Forsen, J. O. Tegenfeldt, A. A> Zakharov, L. Montelius, Fabrication and chacterization of a molecular adhesive layer for micro- and nanofabricated electrochemical electrodes, Microelectronic Engineering 67-68 (2003) 887-892.
[P8] U.S. Pat. No. 6,408,878.
[P9] U.S. Pat. No. 6,793,753.
[P10] U.S. Pat. No. 6,899,137.
[P11] U.S. Pat. No. 6,929,030.
[P12] U.S. Pat. No. 6,540,895.
[P13] U.S. Pat. No. 7,040,338.
[P14] U.S. Pat. No. 7,144,616.
[P15] U.S. Pat. No. 7,169,314.
[P16] U.S. Pat. No. 7,216,671.
[P17] U.S. Pat. No. 7,214,298.
[P18] Chun-Min Lo, Hong-Bei Wang, Micah Dembo, and Yu-li Wang, Cell Movement is Guided by the Rigidity of the Substrate, Biophyscial Journal, Volume 79, pp 144-152 (July 2000).
[P19] John L. Tan, Joe Tien, Dana M. Pirone, Darren S. Gray, Kiran Bhadriraju, and Christopher S. Chen, Cells lying on a bid of microneedles: An approach to isolate mechanical force, Proceedings of the National Academy of Sciences, vol. 100, no. 4, pp 1484-1489 (Feb. 18, 2003).
[P20] Arkles, B., Tailoring Inorganic Surfaces with Organosilanes, Am. Inst. Chem. Eng. Proc., 69 (December 1976).
[P21] Arkles, B., Tailoring Surfaces with Silanes, CHEMTECH, 7(12), 766, (1977).
[P22] Arkles, B. C., Brinigar, W. S., Method of Siliconization of Surfaces with Lower Alkyl Silanes, U.S. Pat. No. 4,711,820, (Dec. 8, 1987).
[P23] Van Ruitenbeek, J. M., Alvarez, A., Pineyro, I., Grahman, C., Joyez, P., Devoret, M. H., Esteve, D., and Urbina, C. Adjustable nanofabricated atomic sized contacts. *Review of Scientific Instruments,* 67, 108 (1996).
[CIT 1] MicroCal, LLC. 22 Industrial Drive East, Northampton, Mass. 01060.
[CIT 2] Johannessen, E A, Weaver, J M, Cobbold, P H, Cooper, J M. Heat conduction nanocalorimeter for pl-scale single cell measurement. *Appl. Phys. Lett.,* 80, 2029 (2002).
[CIT 3] Zhang, Y, and Tadigadapa, S. Calorimetric biosensors with integrated microfluidics channels. *Biosensors and Bioelectronics,* 19, 1733 (2004).

What is claimed is:

1. A microfluidic embedded vacuum insulated biocalorimeter comprising:
   a calorimeter chamber comprising a parylene membrane, wherein both sides of the calorimeter chamber are under vacuum during measurement of a sample;
   a microfluidic channel used to deliver a sample to the calorimeter chamber, wherein the microfluidic channel is built from the parylene membrane; and
   a thermopile, used as a thermometer, located between two layers of the parylene membrane and protected from the sample.

2. The biocalorimeter of claim 1 wherein a PDMS (polydimethylsiloxane) peristaltic pump is used to move the sample in liquid along the microfluidic channel.

3. The biocalorimeter of claim 1, wherein the calorimeter chamber comprises:
   a first region adjacent the parylene member defined by SU-8 on a first side and glass on a second side; and
   a second region adjacent the parylene member formed by potassium hydroxide (KOH) etching for a SiN (Silicon nitride) membrane that is sealed.

4. The biocalorimeter of claim 1, wherein multiple layers of vacuum provide insulation of the sample.

5. The biocalorimeter of claim 1, wherein the thermopile comprises an AuNi alloy (Gold Nickel).

6. A method for measuring an enthalpy change of a sample in a microfluidic embedded vacuum insulated biocalorimeter, comprising:
   creating a calorimeter chamber comprising a parylene membrane, wherein both sides of the calorimeter chamber are under vacuum during measurement of the sample;
   creating a microfluidic channel used to deliver a sample to the calorimeter chamber, wherein the microfluidic channel is built from the parylene membrane; and
   encapsulating a thermopile, used as a thermometer, between two layers of the parylene membrane and protected from the sample; and
   measuring the enthalpy change of the sample in the calorimeter chamber.

7. The method of claim 6 further comprising moving the sample in liquid along the microfluidic channel utilizing a PDMS (polydimethylsiloxane) peristaltic pump.

8. The method of claim 6, wherein the calorimeter chamber is created by:
   defining a first region adjacent the parylene member by SU-8 on a first side and glass on a second side; and
   forming a second region adjacent the parylene member by potassium hydroxide (KOH) etching for a SiN (Silicon nitride) membrane that is sealed.

9. The method of claim 6, further comprising insulating the sample using multiple layers of vacuum.

10. The method of claim 6, wherein the thermopile comprises an AuNi alloy (Gold Nickel).

* * * * *